US012590128B2

(12) United States Patent
Kim et al.

(10) Patent No.: US 12,590,128 B2
(45) Date of Patent: Mar. 31, 2026

(54) ACETOHYDROXY ACID SYNTHASE VARIANT AND MICROORGANISM INCLUDING THE SAME

(71) Applicant: CJ CHEILJEDANG CORPORATION, Seoul (KR)

(72) Inventors: Kyungrim Kim, Seoul (KR); Tae Yeon Kim, Seoul (KR); Imsang Lee, Seoul (KR); Kwang Woo Lee, Seoul (KR); Heeyeong Kim, Seoul (KR); Kwang Soo Shin, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 953 days.

(21) Appl. No.: 17/778,810

(22) PCT Filed: Jun. 10, 2020

(86) PCT No.: PCT/KR2020/007529
§ 371 (c)(1),
(2) Date: May 20, 2022

(87) PCT Pub. No.: WO2021/101000
PCT Pub. Date: May 27, 2021

(65) Prior Publication Data
US 2023/0008411 A1    Jan. 12, 2023
US 2023/0203106 A1    Jun. 29, 2023

(30) Foreign Application Priority Data

Nov. 22, 2019    (KR) ........................ 10-2019-0151672

(51) Int. Cl.
C07K 14/34     (2006.01)
C07K 14/245    (2006.01)
C12N 1/20      (2006.01)

(52) U.S. Cl.
CPC ............ *C07K 14/34* (2013.01); *C07K 14/245* (2013.01); *C12N 1/20* (2013.01)

(58) Field of Classification Search
CPC ...................................................... C07K 14/34
See application file for complete search history.

(56) References Cited

U.S. PATENT DOCUMENTS

| | | | |
|---|---|---|---|
| 6,576,455 B1 * | 6/2003 | Kakefuda | ................ C12N 9/88 435/189 |
| 2006/0156427 A1 | 7/2006 | Kakefuda et al. | |
| 2009/0205064 A1 | 8/2009 | Schopke et al. | |
| 2010/0086966 A1 | 4/2010 | Patek et al. | |
| 2011/0053777 A1 | 3/2011 | Oard et al. | |
| 2014/0335574 A1 | 11/2014 | Sycheva et al. | |

FOREIGN PATENT DOCUMENTS

| | | |
|---|---|---|
| EP | 3178926 A1 | 6/2017 |
| EP | 3553171 A2 | 10/2019 |
| KR | 10-2006-0024437 A | 3/2006 |
| KR | 10-2013-0083690 A | 7/2013 |
| KR | 10-2016-0015298 A | 2/2016 |
| KR | 10-2017-0047725 A | 5/2017 |
| KR | 10-2019-0037224 A | 4/2019 |
| WO | 01/09286 A1 | 2/2001 |

OTHER PUBLICATIONS

Guo et al., "Analysis of acetohydroxyacid synthase variants from branched-chain amino acids-producing strains and their effects on the synthesis of branched-chain amino acids in Corynebacterium glutamicum," Protein Expression and Purification, 109: 106-112 (2015).
International Search Report issued in corresponding International Patent Application No. PCT/KR2020/007529 dated Oct. 15, 2020.
Extended European Search Report issued in corresponding European Patent Application No. 20890887.1 dated Oct. 10, 2022.

* cited by examiner

*Primary Examiner* — Suzanne M Noakes
(74) *Attorney, Agent, or Firm* — Morgan, Lewis & Bockius LLP

(57)     ABSTRACT
The present disclosure relates to an acetohydroxy acid synthase variant, a polynucleotide encoding the variant, a microorganism including the variant, and a method of producing L-isoleucine using the microorganism.

20 Claims, No Drawings

Specification includes a Sequence Listing.

SEQUENCE LISTING

```
<160> NUMBER OF SEQ ID NOS: 78

<210> SEQ ID NO 1
<211> LENGTH: 626
<212> TYPE: PRT
<213> ORGANISM: Artificial Sequence
<220> FEATURE:
<223> OTHER INFORMATION: acetohydroxy acid synthase, AHAS

<400> SEQUENCE: 1

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Lys Ala Ile
            20                  25                  30

Val Arg Ser Leu Glu Glu Leu Asn Ala Asp Ile Val Phe Gly Ile Pro
        35                  40                  45

Gly Gly Ala Val Leu Pro Val Tyr Asp Pro Leu Tyr Ser Ser Thr Lys
    50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Thr
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Gln Glu Ala Asp Ile Arg Gly Ile Thr
    130                 135                 140

Met Pro Val Thr Lys His Asn Phe Met Val Thr Asn Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ala Lys Lys Pro Val Leu Tyr Val Gly Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
                260                 265                 270

Leu His Met Gly Met Pro Gly Met His Gly Thr Val Ser Ala Val Gly
            275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
```

```
305                 310                 315                 320

Ile His Ala Asp Ile Asp Pro Ala Glu Ile Gly Lys Ile Lys Gln Val
            325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
            355                 360                 365

Val Asp Tyr Leu Lys Gly Leu Lys Ala Arg Phe Pro Arg Gly Tyr Asp
    370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
            435                 440                 445

Ala Leu Gly Ala Lys Ala Gly Ala Pro Asp Lys Glu Val Trp Ala Ile
    450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
            515                 520                 525

Thr Leu Ser Glu Gly Leu Gly Cys Val Ala Ile Arg Val Thr Lys Ala
    530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
            595                 600                 605

Asp Ile His Glu Ala Val Ser Asp Ile Asp Ala Ala Val Glu Ser Thr
    610                 615                 620

Glu Ala
625
```

```
<210> SEQ ID NO 2
<211> LENGTH: 1881
<212> TYPE: DNA
<213> ORGANISM: Artificial Sequence
<220> FEATURE:
<223> OTHER INFORMATION: ilvB variant n.t

<400> SEQUENCE: 2
gtgaatgtgg cagcttctca acagcccact cccgccacgg ttgcaagccg tggtcgatcc      60 gccgccctg agcggatgac aggtgcaaag gcaattgttc gatcgctcga ggagcttaac     120
gccgacatcg tgttcggtat tcctggtggt gcggtgctac cggtgtatga cccgctctat     180
tcctccacaa aggtgcgcca cgtcttggtg cgccacgagc agggcgcagg ccacgcagca     240
```

```
accggctacg cgcaggttac tggacgcgtt ggcgtctgca ttgcaacctc tggcccagga      300
gcaaccaact tggttacccc aatcgctgat gcaaacttgg actccgttcc catggttgcc      360
atcaccggcc aggtcggaag tggcctgctg ggtaccgacg ctttcaacga agccgatatc      420
cgcggcatca ccatgccagt gaccaagcac aacttcatgg tcaccaaccc taacgacatt      480
ccacaggcat tggctgaggc attccacctc gcgattactg tcgccctggg ccctgttctg      540
gtggatattc ctaaggatgt ccagaacgct gaattggatt tcgtctggcc accaaagatc      600
gacctgccag gctaccgccc agtttcaaca ccacatgctc gccagatcga gcaggcagtc      660
aagctgatcg tggaggccaa gaagcccgtc ctttacgttg tggtggcgt aatcaaggct      720 gacgcacacg aagagcttcg tgcgttcgct gagtacaccg gcatcccagt tgtcaccacc      780
ttgatggctt tgggtacttt cccagagtct cacgagctgc acatgggtat gccaggcatg      840
catggcactg tgtccgctgt tggtgcactg cagcgcagcg acctgctgat tgctatcggc      900
tcccgctttg atgaccgcgt caccggtgac gttgacacct cgcgcctga cgccaagatc      960 attcacgccg acattgatcc tgccgaaatc ggcaagatca agcaggttga ggttccaatc     1020
gtgggcgatg cccgcgaagt tcttgctcgt ctgctggaaa ccaccaaggc aagcaaggca     1080
gagaccgagg acatctccga gtgggttgac tacctcaagg gcctcaaggc acgtttcccg     1140
cgtggctacg acgagcagcc aggcgatctg ctggcaccac agtttgtcat tgaaccctg     1200 tccaaggaag ttggccccga cgcaatttac tgcgccggcg ttggccagca ccaaatgtgg     1260
gcagctcagt tcgttgactt tgaaaagcca cgcacctggc tcaactccgg tggactgggc     1320
accatgggct acgcagttcc tgcggccctt ggagcaaagg ctggcgcacc tgacaaggaa     1380
gtctgggcta tcgacggcga cggctgtttc cagatgacca accaggaact caccaccgcc     1440
gcagttgaag gtttccccat taagatcgca ctaatcaaca acgaaacct gggcatggtt     1500 cgccaatggc agaccctatt ctatgaagga cggtactcaa atactaaact tcgtaaccag     1560
ggcgagtaca tgcccgactt tgttaccctt tctgagggac ttggctgtgt tgccatccgc     1620
gtcaccaaag cggaggaagt actgccagcc atccaaaagg ctcgagagat caacgaccgc     1680
ccagtagtca tcgacttcat cgtcggtgaa gacgcacagg tatggccaat ggtgtctgct     1740
ggatcatcca actccgatat ccagtacgca ctcggattgc gcccattctt tgatggtgat     1800
gaatctgcag cagaagatcc tgccgacatt cacgaagccg tcagcgacat tgatgccgcc     1860
gttgaatcga ccgaggcata a                                               1881
```

<210> SEQ ID NO 3
<211> LENGTH: 23
<212> TYPE: DNA
<213> ORGANISM: Artificial Sequence
<220> FEATURE:
<223> OTHER INFORMATION: primer

<400> SEQUENCE: 3

```
attctagagg ccaagaagtc cgc                                               23
```

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4

```
cttgttgctg ctacacacat cgagtttcc                                    29

<210> SEQ ID NO 5
<211> LENGTH: 29
<212> TYPE: DNA
<213> ORGANISM: Artificial Sequence
<220> FEATURE:
<223> OTHER INFORMATION: primer

<400> SEQUENCE: 5
tgtagcagca acaagatttt ggcaaaatg                                    29

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
attctagagc cgaacggcgc ccc                                          23

<210> SEQ ID NO 7
<211> LENGTH: 1881
<212> TYPE: DNA
<213> ORGANISM: Artificial Sequence
<220> FEATURE:
<223> OTHER INFORMATION: Corynebacterium glutamicum ATCC 13032 hom/ilvA
      variant

<400> SEQUENCE: 7
gtgaatgtgg cagcttctca acagcccact cccgccacgg ttgcaagccg tggtcgatcc    60
gccgcccctg agcggatgac aggtgcaaag gcaattgttc gatcgctcga ggagcttaac   120
gccgacatcg tgttcggtat tcctggtggt gcggtgctac cggtgtatga cccgctctat   180
tcctccacaa aggtgcgcca cgtcttggtg cgccacgagc agggcgcagg ccacgcagca   240
accggctacg cgcaggttac tggacgcgtt ggcgtctgca ttgcaacctc tggcccagga   300
gcaaccaact tggttacccc aatcgctgat gcaaacttgg actccgttcc catggttgcc   360
atcaccggcc aggtcggaag tggcctgctg ggtaccgacg ctttccagga agccgatatc   420
cgcggcatca ccatgccagt gaccaagcac aacttcatgg tcaccaaccc taacgacatt   480
ccacaggcat tggctgaggc attccacctc gcgattactg tcgccctggg ccctgttctg   540
gtggatattc ctaaggatgt ccagaacgct gaattggatt tcgtctggcc accaaagatc   600
gacctgccag gctaccgccc agtttcaaca ccacatgctc gccagatcga gcaggcagtc   660
aagctgatcg gtgaggccaa gaagcccgtc ctttacgttg gtggtggcgt aatcaaggct   720
gacgcacacg aagagcttcg tgcgttcgct gagtacaccg gcatcccagt tgtcaccacc   780
ttgatggctt tgggtacttt cccagagtct cacgagctgc acatgggtat gccaggcatg   840
catggcactg tgtccgctgt tggtgcactg cagcgcagcg acctgctgat tgctatcggc   900
tcccgctttg atgaccgcgt caccggtgac gttgacacct cgcgcctga cgccaagatc   960 attcacgccg acattgatcc tgccgaaatc ggcaagatca agcaggttga ggttccaatc   1020
gtgggcgatg cccgcgaagt tcttgctcgt ctgctggaaa ccaccaaggc aagcaaggca   1080
gagaccgagg acatctccga gtgggttgac tacctcaagg cctcaaggc acgtttcccg   1140 cgtggctacg acgagcagcc aggcgatctg ctggcaccac agtttgtcat tgaaaccctg   1200
tccaaggaag ttggccccga cgcaatttac tgcgccggcg ttggccagca ccaaatgtgg   1260
```

```
gcagctcagt tcgttgactt tgaaaagcca cgcacctggc tcaactccgg tggactgggc    1320
accatgggct acgcagttcc tgcggccctt ggagcaaagg ctggcgcacc tgacaaggaa    1380
gtctgggcta tcgacggcga cggctgtttc cagatgacca accaggaact caccaccgcc    1440
gcagttgaag gtttccccat taagatcgca ctaatcaaca cggaaacct gggcatggtt     1500 cgccaatggc agaccctatt ctatgaagga cggtactcaa atactaaact tcgtaaccag    1560
ggcgagtaca tgcccgactt tgttaccctt tctgagggac ttggctgtgt tgccatccgc    1620
gtcaccaaag cggaggaagt actgccagcc atccaaaagg ctcgagagat caacgaccgc    1680
ccagtagtca tcgacttcat cgtcggtgaa gacgcacagg tatggccaat ggtgtctgct    1740
ggatcatcca actccgatat ccagtacgca ctcggattgc gcccattctt tgatggtgat    1800
gaatctgcag cagaagatcc tgccgacatt cacgaagccg tcagcgacat tgatgccgcc    1860
gttgaatcga ccgaggcata a                                            1881
```

```
<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
tccggatcct gacacaccat gaccattatt c                                  31

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
tccggatccc ttatgtacaa agtgcacagc                                    30

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
cttcgttgaa agcgtcggta cccag                                         25

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
ctttcaacga agccgatatc cgcgg                                         25

<210> SEQ ID NO 12
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 12
```

-continued

```
Met Asn Val Ala Ala Ser Gln Gln Pro Thr Pro Ala Thr Val Ala Ser
1               5               10              15

Arg Gly Arg Ser Ala Ala Pro Glu Arg Met Thr Gly Ala Lys Ala Ile
            20              25              30

Val Arg Ser Leu Glu Glu Leu Asn Ala Asp Ile Val Phe Gly Ile Pro
        35              40              45

Gly Gly Ala Val Leu Pro Val Tyr Asp Pro Leu Tyr Ser Ser Thr Lys
    50              55              60

Val Arg His Val Leu Val Arg His Glu Gln Gly Ala Gly His Ala Ala
65              70              75              80

Thr Gly Tyr Ala Gln Val Thr Gly Arg Val Gly Val Cys Ile Ala Thr
            85              90              95

Ser Gly Pro Gly Ala Thr Asn Leu Val Thr Pro Ile Ala Asp Ala Asn
        100             105             110

Leu Asp Ser Val Pro Met Val Ala Ile Thr Gly Gln Val Gly Ser Gly
    115             120             125

Leu Leu Gly Thr Asp Ala Phe Asn Glu Ala Asp Ile Arg Gly Ile Thr
    130             135             140

Met Pro Val Thr Lys His Asn Phe Met Val Thr Asn Pro Asn Asp Ile
145             150             155             160

Pro Gln Ala Leu Ala Glu Ala Phe His Leu Ala Ile Thr Gly Arg Pro
            165             170             175

Gly Pro Val Leu Val Asp Ile Pro Lys Asp Val Gln Asn Ala Glu Leu
        180             185             190

Asp Phe Val Trp Pro Pro Lys Ile Asp Leu Pro Gly Tyr Arg Pro Val
        195             200             205

Ser Thr Pro His Ala Arg Gln Ile Glu Gln Ala Val Lys Leu Ile Gly
    210             215             220

Glu Ala Lys Lys Pro Val Leu Tyr Val Gly Gly Gly Val Ile Lys Ala
225             230             235             240

Asp Ala His Glu Glu Leu Arg Ala Phe Ala Glu Tyr Thr Gly Ile Pro
            245             250             255

Val Val Thr Thr Leu Met Ala Leu Gly Thr Phe Pro Glu Ser His Glu
        260             265             270

Leu His Met Gly Met Pro Gly Met His Gly Thr Val Ser Ala Val Gly
    275             280             285

Ala Leu Gln Arg Ser Asp Leu Leu Ile Ala Ile Gly Ser Arg Phe Asp
    290             295             300

Asp Arg Val Thr Gly Asp Val Asp Thr Phe Ala Pro Asp Ala Lys Ile
305             310             315             320

Ile His Ala Asp Ile Asp Pro Ala Glu Ile Gly Lys Ile Lys Gln Val
            325             330             335

Glu Val Pro Ile Val Gly Asp Ala Arg Glu Val Leu Ala Arg Leu Leu
            340             345             350

Glu Thr Thr Lys Ala Ser Lys Ala Glu Thr Glu Asp Ile Ser Glu Trp
        355             360             365

Val Asp Tyr Leu Lys Gly Leu Lys Ala Arg Phe Pro Arg Gly Tyr Asp
    370             375             380

Glu Gln Pro Gly Asp Leu Leu Ala Pro Gln Phe Val Ile Glu Thr Leu
385             390             395             400

Ser Lys Glu Val Gly Pro Asp Ala Ile Tyr Cys Ala Gly Val Gly Gln
            405             410             415
```

-continued

```
His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
            435                 440                 445

Ala Leu Gly Ala Lys Ala Gly Ala Pro Asp Lys Glu Val Trp Ala Ile
            450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                    485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
            515                 520                 525

Thr Leu Ser Glu Gly Leu Gly Cys Val Ala Ile Arg Val Thr Lys Ala
            530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                    565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
            595                 600                 605

Asp Ile His Glu Ala Val Ser Asp Ile Asp Ala Ala Val Glu Ser Thr
            610                 615                 620

Glu Ala
625
```

```
<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
tcggcttcgc ggaaagcgtc ggtac                                              25

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
cgctttccgc gaagccgata tccgc                                              25

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
cggcttcgaa gaaagcgtcg gtac                                               24
```

-continued

```
<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
cgctttcttc gaagccgata tccgc                                    25

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
cggcttcgga gaaagcgtcg gtac                                     24

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
cgctttctcc gaagccgata tccgc                                    25

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
cggcttcgta gaaagcgtcg gtac                                     24

<210> SEQ ID NO 20
<211> LENGTH: 25
<212> TYPE: DNA
<213> ORGANISM: Artificial Sequence
<220> FEATURE:
<223> OTHER INFORMATION: primer

<400> SEQUENCE: 20
cgctttctac gaagccgata tccgc                                    25

<210> SEQ ID NO 21
<211> LENGTH: 24
<212> TYPE: DNA
<213> ORGANISM: Artificial Sequence
<220> FEATURE:
<223> OTHER INFORMATION: primer

<400> SEQUENCE: 21
cggcttcgca gaaagcgtcg gtac                                     24

<210> SEQ ID NO 22
<211> LENGTH: 25
<212> TYPE: DNA
<213> ORGANISM: Artificial Sequence
<220> FEATURE:
<223> OTHER INFORMATION: primer
```

<400> SEQUENCE: 22
cgctttctgc gaagccgata tccgc                                      25

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
cggcttctgg gaaagcgtcg gtac                                       24

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
cgctttccca gaagccgata tccgc                                      25

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
cggcttcgtg gaaagcgtcg gtac                                       24

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
cgctttccac gaagccgata tccgc                                      25

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
cggcttccag gaaagcgtcg gtac                                       24

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
cgctttcctg gaagccgata tccgc                                      25

<210> SEQ ID NO 29
<211> LENGTH: 24

-continued

```
<212> TYPE: DNA
<213> ORGANISM: Artificial Sequence
<220> FEATURE:
<223> OTHER INFORMATION: primer

<400> SEQUENCE: 29
cggcttcgat gaaagcgtcg gtac                                          24

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
cgctttcatc gaagccgata tccgc                                         25

<210> SEQ ID NO 31
<211> LENGTH: 24
<212> TYPE: DNA
<213> ORGANISM: Artificial Sequence
<220> FEATURE:
<223> OTHER INFORMATION: primer

<400> SEQUENCE: 31
cggcttcggt gaaagcgtcg gtac                                          24

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
cgctttcacc gaagccgata tccgc                                         25

<210> SEQ ID NO 33
<211> LENGTH: 24
<212> TYPE: DNA
<213> ORGANISM: Artificial Sequence
<220> FEATURE:
<223> OTHER INFORMATION: primer

<400> SEQUENCE: 33
cggcttcctt gaaagcgtcg gtac                                          24

<210> SEQ ID NO 34
<211> LENGTH: 25
<212> TYPE: DNA
<213> ORGANISM: Artificial Sequence
<220> FEATURE:
<223> OTHER INFORMATION: primer

<400> SEQUENCE: 34
cgctttcaag gaagccgata tccgc                                         25

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
```

-continued cggcttcaac gaaagcgtcg gtac                                        24

<210> SEQ ID NO 36
<211> LENGTH: 25
<212> TYPE: DNA
<213> ORGANISM: Artificial Sequence
<220> FEATURE:
<223> OTHER INFORMATION: primer

<400> SEQUENCE: 36
cgctttcgtt gaagccgata tccgc                                       25

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
cggcttcagc gaaagcgtcg gtac                                        24

<210> SEQ ID NO 38
<211> LENGTH: 25
<212> TYPE: DNA
<213> ORGANISM: Artificial Sequence
<220> FEATURE:
<223> OTHER INFORMATION: primer

<400> SEQUENCE: 38
cgctttcgct gaagccgata tccgc                                       25

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
cggcttcgtc gaaagcgtcg gtac                                        24

<210> SEQ ID NO 40
<211> LENGTH: 25
<212> TYPE: DNA
<213> ORGANISM: Artificial Sequence
<220> FEATURE:
<223> OTHER INFORMATION: primer

<400> SEQUENCE: 40
cgctttcgac gaagccgata tccgc                                       25

<210> SEQ ID NO 41
<211> LENGTH: 24
<212> TYPE: DNA
<213> ORGANISM: Artificial Sequence
<220> FEATURE:
<223> OTHER INFORMATION: primer

<400> SEQUENCE: 41
cggcttcctc gaaagcgtcg gtac                                        24

<210> SEQ ID NO 42
<211> LENGTH: 25
<212> TYPE: DNA
<213> ORGANISM: Artificial Sequence -continued
<220> FEATURE:
<223> OTHER INFORMATION: primer

<400> SEQUENCE: 42
cgctttcgag gaagccgata tccgc                                         25

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
cggcttcgcc gaaagcgtcg gtac                                          24

<210> SEQ ID NO 44
<211> LENGTH: 25
<212> TYPE: DNA
<213> ORGANISM: Artificial Sequence
<220> FEATURE:
<223> OTHER INFORMATION: primer

<400> SEQUENCE: 44
cgctttcggc gaagccgata tccgc                                         25

<210> SEQ ID NO 45
<211> LENGTH: 24
<212> TYPE: DNA
<213> ORGANISM: Artificial Sequence
<220> FEATURE:
<223> OTHER INFORMATION: primer

<400> SEQUENCE: 45
cggcttccca gaaagcgtcg gtac                                          24

<210> SEQ ID NO 46
<211> LENGTH: 25
<212> TYPE: DNA
<213> ORGANISM: Artificial Sequence
<220> FEATURE:
<223> OTHER INFORMATION: primer

<400> SEQUENCE: 46
cgctttctgg gaagccgata tccgc                                         25

<210> SEQ ID NO 47
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 47

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Lys Ala Ile
            20                  25                  30

Val Arg Ser Leu Glu Glu Leu Asn Ala Asp Ile Val Phe Gly Ile Pro
        35                  40                  45

Gly Gly Ala Val Leu Pro Val Tyr Asp Pro Leu Tyr Ser Ser Thr Lys
    50                  55                  60

Val Arg His Val Leu Val Arg His Glu Gln Gly Ala Gly His Ala Ala
65                  70                  75                  80

47
48

-continued

```
Thr Gly Tyr Ala Gln Val Thr Gly Arg Val Gly Val Cys Ile Ala Thr
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Arg Glu Ala Asp Ile Arg Gly Ile Thr
    130                 135                 140

Met Pro Val Thr Lys His Asn Phe Met Val Thr Asn Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ala Lys Lys Pro Val Leu Tyr Val Gly Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
        275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
        355                 360                 365

Val Asp Tyr Leu Lys Gly Leu Lys Ala Arg Phe Pro Arg Gly Tyr Asp
    370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
        435                 440                 445

Ala Leu Gly Ala Lys Ala Gly Ala Pro Asp Lys Glu Val Trp Ala Ile
    450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495
```

-continued

```
Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
            515                 520                 525

Thr Leu Ser Glu Gly Leu Gly Cys Val Ala Ile Arg Val Thr Lys Ala
            530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
            595                 600                 605

Asp Ile His Glu Ala Val Ser Asp Ile Asp Ala Ala Val Glu Ser Thr
            610                 615                 620

Glu Ala
625

<210> SEQ ID NO 48
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 48

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Lys Ala Ile
            20                  25                  30

Val Arg Ser Leu Glu Glu Leu Asn Ala Asp Ile Val Phe Gly Ile Pro
            35                  40                  45

Gly Gly Ala Val Leu Pro Val Tyr Asp Pro Leu Tyr Ser Ser Thr Lys
        50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Thr
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
            115                 120                 125

Leu Leu Gly Thr Asp Ala Phe Phe Glu Ala Asp Ile Arg Gly Ile Thr
            130                 135                 140

Met Pro Val Thr Lys His Asn Phe Met Val Thr Asn Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
            195                 200                 205

Ser Thr Pro His Ala Arg Gln Ile Glu Gln Ala Val Lys Leu Ile Gly
            210                 215                 220
```

-continued

```
Glu Ala Lys Lys Pro Val Leu Tyr Val Gly Gly Gly Val Ile Lys Ala
225             230             235             240

Asp Ala His Glu Glu Leu Arg Ala Phe Ala Glu Tyr Thr Gly Ile Pro
            245             250             255

Val Val Thr Thr Leu Met Ala Leu Gly Thr Phe Pro Glu Ser His Glu
            260             265             270

Leu His Met Gly Met Pro Gly Met His Gly Thr Val Ser Ala Val Gly
        275             280             285

Ala Leu Gln Arg Ser Asp Leu Leu Ile Ala Ile Gly Ser Arg Phe Asp
        290             295             300

Asp Arg Val Thr Gly Asp Val Asp Thr Phe Ala Pro Asp Ala Lys Ile
305             310             315             320

Ile His Ala Asp Ile Asp Pro Ala Glu Ile Gly Lys Ile Lys Gln Val
            325             330             335

Glu Val Pro Ile Val Gly Asp Ala Arg Glu Val Leu Ala Arg Leu Leu
            340             345             350

Glu Thr Thr Lys Ala Ser Lys Ala Glu Thr Glu Asp Ile Ser Glu Trp
        355             360             365

Val Asp Tyr Leu Lys Gly Leu Lys Ala Arg Phe Pro Arg Gly Tyr Asp
        370             375             380

Glu Gln Pro Gly Asp Leu Leu Ala Pro Gln Phe Val Ile Glu Thr Leu
385             390             395             400

Ser Lys Glu Val Gly Pro Asp Ala Ile Tyr Cys Ala Gly Val Gly Gln
            405             410             415

His Gln Met Trp Ala Ala Gln Phe Val Asp Phe Glu Lys Pro Arg Thr
            420             425             430

Trp Leu Asn Ser Gly Gly Leu Gly Thr Met Gly Tyr Ala Val Pro Ala
        435             440             445

Ala Leu Gly Ala Lys Ala Gly Ala Pro Asp Lys Glu Val Trp Ala Ile
        450             455             460

Asp Gly Asp Gly Cys Phe Gln Met Thr Asn Gln Glu Leu Thr Thr Ala
465             470             475             480

Ala Val Glu Gly Phe Pro Ile Lys Ile Ala Leu Ile Asn Asn Gly Asn
            485             490             495

Leu Gly Met Val Arg Gln Trp Gln Thr Leu Phe Tyr Glu Gly Arg Tyr
            500             505             510

Ser Asn Thr Lys Leu Arg Asn Gln Gly Glu Tyr Met Pro Asp Phe Val
        515             520             525

Thr Leu Ser Glu Gly Leu Gly Cys Val Ala Ile Arg Val Thr Lys Ala
        530             535             540

Glu Glu Val Leu Pro Ala Ile Gln Lys Ala Arg Glu Ile Asn Asp Arg
545             550             555             560

Pro Val Val Ile Asp Phe Ile Val Gly Glu Asp Ala Gln Val Trp Pro
            565             570             575

Met Val Ser Ala Gly Ser Ser Asn Ser Asp Ile Gln Tyr Ala Leu Gly
            580             585             590

Leu Arg Pro Phe Phe Asp Gly Asp Glu Ser Ala Ala Glu Asp Pro Ala
        595             600             605

Asp Ile His Glu Ala Val Ser Asp Ile Asp Ala Ala Val Glu Ser Thr
        610             615             620

Glu Ala
625
```

```
<210> SEQ ID NO 49
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 49

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Lys Ala Ile
            20                  25                  30

Val Arg Ser Leu Glu Glu Leu Asn Ala Asp Ile Val Phe Gly Ile Pro
        35                  40                  45

Gly Gly Ala Val Leu Pro Val Tyr Asp Pro Leu Tyr Ser Ser Thr Lys
    50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Thr
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Ser Glu Ala Asp Ile Arg Gly Ile Thr
    130                 135                 140

Met Pro Val Thr Lys His Asn Phe Met Val Thr Asn Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ala Lys Lys Pro Val Leu Tyr Val Gly Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
        275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
        355                 360                 365

Val Asp Tyr Leu Lys Gly Leu Lys Ala Arg Phe Pro Arg Gly Tyr Asp
```

-continued

```
          370              375              380
Glu Gln Pro Gly Asp Leu Leu Ala Pro Gln Phe Val Ile Glu Thr Leu
385              390              395              400

Ser Lys Glu Val Gly Pro Asp Ala Ile Tyr Cys Ala Gly Val Gly Gln
                 405              410              415

His Gln Met Trp Ala Ala Gln Phe Val Asp Phe Glu Lys Pro Arg Thr
             420              425              430

Trp Leu Asn Ser Gly Gly Leu Gly Thr Met Gly Tyr Ala Val Pro Ala
             435              440              445

Ala Leu Gly Ala Lys Ala Gly Ala Pro Asp Lys Glu Val Trp Ala Ile
         450              455              460

Asp Gly Asp Gly Cys Phe Gln Met Thr Asn Gln Glu Leu Thr Thr Ala
465              470              475              480

Ala Val Glu Gly Phe Pro Ile Lys Ile Ala Leu Ile Asn Asn Gly Asn
                 485              490              495

Leu Gly Met Val Arg Gln Trp Gln Thr Leu Phe Tyr Glu Gly Arg Tyr
             500              505              510

Ser Asn Thr Lys Leu Arg Asn Gln Gly Glu Tyr Met Pro Asp Phe Val
             515              520              525

Thr Leu Ser Glu Gly Leu Gly Cys Val Ala Ile Arg Val Thr Lys Ala
         530              535              540

Glu Glu Val Leu Pro Ala Ile Gln Lys Ala Arg Glu Ile Asn Asp Arg
545              550              555              560

Pro Val Val Ile Asp Phe Ile Val Gly Glu Asp Ala Gln Val Trp Pro
                 565              570              575

Met Val Ser Ala Gly Ser Ser Asn Ser Asp Ile Gln Tyr Ala Leu Gly
             580              585              590

Leu Arg Pro Phe Phe Asp Gly Asp Glu Ser Ala Ala Glu Asp Pro Ala
             595              600              605

Asp Ile His Glu Ala Val Ser Asp Ile Asp Ala Ala Val Glu Ser Thr
         610              615              620

Glu Ala
625
```

```
<210> SEQ ID NO 50
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 50

Met Asn Val Ala Ala Ser Gln Gln Pro Thr Pro Ala Thr Val Ala Ser
1               5               10               15

Arg Gly Arg Ser Ala Ala Pro Glu Arg Met Thr Gly Ala Lys Ala Ile
                 20               25               30

Val Arg Ser Leu Glu Glu Leu Asn Ala Asp Ile Val Phe Gly Ile Pro
             35               40               45

Gly Gly Ala Val Leu Pro Val Tyr Asp Pro Leu Tyr Ser Ser Thr Lys
         50               55               60

Val Arg His Val Leu Val Arg His Glu Gln Gly Ala Gly His Ala Ala
65               70               75               80

Thr Gly Tyr Ala Gln Val Thr Gly Arg Val Gly Val Cys Ile Ala Thr
                 85               90               95

Ser Gly Pro Gly Ala Thr Asn Leu Val Thr Pro Ile Ala Asp Ala Asn
```

-continued

```
                100              105              110

Leu Asp Ser Val Pro Met Val Ala Ile Thr Gly Gln Val Gly Ser Gly
        115              120              125

Leu Leu Gly Thr Asp Ala Phe Tyr Glu Ala Asp Ile Arg Gly Ile Thr
    130              135              140

Met Pro Val Thr Lys His Asn Phe Met Val Thr Asn Pro Asn Asp Ile
145              150              155              160

Pro Gln Ala Leu Ala Glu Ala Phe His Leu Ala Ile Thr Gly Arg Pro
            165              170              175

Gly Pro Val Leu Val Asp Ile Pro Lys Asp Val Gln Asn Ala Glu Leu
            180              185              190

Asp Phe Val Trp Pro Pro Lys Ile Asp Leu Pro Gly Tyr Arg Pro Val
            195              200              205

Ser Thr Pro His Ala Arg Gln Ile Glu Gln Ala Val Lys Leu Ile Gly
        210              215              220

Glu Ala Lys Lys Pro Val Leu Tyr Val Gly Gly Gly Val Ile Lys Ala
225              230              235              240

Asp Ala His Glu Glu Leu Arg Ala Phe Ala Glu Tyr Thr Gly Ile Pro
            245              250              255

Val Val Thr Thr Leu Met Ala Leu Gly Thr Phe Pro Glu Ser His Glu
            260              265              270

Leu His Met Gly Met Pro Gly Met His Gly Thr Val Ser Ala Val Gly
        275              280              285

Ala Leu Gln Arg Ser Asp Leu Leu Ile Ala Ile Gly Ser Arg Phe Asp
        290              295              300

Asp Arg Val Thr Gly Asp Val Asp Thr Phe Ala Pro Asp Ala Lys Ile
305              310              315              320

Ile His Ala Asp Ile Asp Pro Ala Glu Ile Gly Lys Ile Lys Gln Val
            325              330              335

Glu Val Pro Ile Val Gly Asp Ala Arg Glu Val Leu Ala Arg Leu Leu
            340              345              350

Glu Thr Thr Lys Ala Ser Lys Ala Glu Thr Glu Asp Ile Ser Glu Trp
        355              360              365

Val Asp Tyr Leu Lys Gly Leu Lys Ala Arg Phe Pro Arg Gly Tyr Asp
    370              375              380

Glu Gln Pro Gly Asp Leu Leu Ala Pro Gln Phe Val Ile Glu Thr Leu
385              390              395              400

Ser Lys Glu Val Gly Pro Asp Ala Ile Tyr Cys Ala Gly Val Gly Gln
            405              410              415

His Gln Met Trp Ala Ala Gln Phe Val Asp Phe Glu Lys Pro Arg Thr
            420              425              430

Trp Leu Asn Ser Gly Gly Leu Gly Thr Met Gly Tyr Ala Val Pro Ala
        435              440              445

Ala Leu Gly Ala Lys Ala Gly Ala Pro Asp Lys Glu Val Trp Ala Ile
    450              455              460

Asp Gly Asp Gly Cys Phe Gln Met Thr Asn Gln Glu Leu Thr Thr Ala
465              470              475              480

Ala Val Glu Gly Phe Pro Ile Lys Ile Ala Leu Ile Asn Asn Gly Asn
            485              490              495

Leu Gly Met Val Arg Gln Trp Gln Thr Leu Phe Tyr Glu Gly Arg Tyr
            500              505              510

Ser Asn Thr Lys Leu Arg Asn Gln Gly Glu Tyr Met Pro Asp Phe Val
        515              520              525
```

-continued

```
Thr Leu Ser Glu Gly Leu Gly Cys Val Ala Ile Arg Val Thr Lys Ala
    530             535             540

Glu Glu Val Leu Pro Ala Ile Gln Lys Ala Arg Glu Ile Asn Asp Arg
545             550             555             560

Pro Val Val Ile Asp Phe Ile Val Gly Glu Asp Ala Gln Val Trp Pro
                565             570             575

Met Val Ser Ala Gly Ser Ser Asn Ser Asp Ile Gln Tyr Ala Leu Gly
            580             585             590

Leu Arg Pro Phe Phe Asp Gly Asp Glu Ser Ala Ala Glu Asp Pro Ala
            595             600             605

Asp Ile His Glu Ala Val Ser Asp Ile Asp Ala Ala Val Glu Ser Thr
    610             615             620

Glu Ala
625

<210> SEQ ID NO 51
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 51

Met Asn Val Ala Ala Ser Gln Gln Pro Thr Pro Ala Thr Val Ala Ser
1               5               10              15

Arg Gly Arg Ser Ala Ala Pro Glu Arg Met Thr Gly Ala Lys Ala Ile
            20              25              30

Val Arg Ser Leu Glu Glu Leu Asn Ala Asp Ile Val Phe Gly Ile Pro
            35              40              45

Gly Gly Ala Val Leu Pro Val Tyr Asp Pro Leu Tyr Ser Ser Thr Lys
    50              55              60

Val Arg His Val Leu Val Arg His Glu Gln Gly Ala Gly His Ala Ala
65              70              75              80

Thr Gly Tyr Ala Gln Val Thr Gly Arg Val Gly Val Cys Ile Ala Thr
            85              90              95

Ser Gly Pro Gly Ala Thr Asn Leu Val Thr Pro Ile Ala Asp Ala Asn
            100             105             110

Leu Asp Ser Val Pro Met Val Ala Ile Thr Gly Gln Val Gly Ser Gly
    115             120             125

Leu Leu Gly Thr Asp Ala Phe Cys Glu Ala Asp Ile Arg Gly Ile Thr
    130             135             140

Met Pro Val Thr Lys His Asn Phe Met Val Thr Asn Pro Asn Asp Ile
145             150             155             160

Pro Gln Ala Leu Ala Glu Ala Phe His Leu Ala Ile Thr Gly Arg Pro
            165             170             175

Gly Pro Val Leu Val Asp Ile Pro Lys Asp Val Gln Asn Ala Glu Leu
            180             185             190

Asp Phe Val Trp Pro Pro Lys Ile Asp Leu Pro Gly Tyr Arg Pro Val
            195             200             205

Ser Thr Pro His Ala Arg Gln Ile Glu Gln Ala Val Lys Leu Ile Gly
    210             215             220

Glu Ala Lys Lys Pro Val Leu Tyr Val Gly Gly Gly Val Ile Lys Ala
225             230             235             240

Asp Ala His Glu Glu Leu Arg Ala Phe Ala Glu Tyr Thr Gly Ile Pro
            245             250             255
```

```
Val Val Thr Thr Leu Met Ala Leu Gly Thr Phe Pro Glu Ser His Glu
        260             265             270

Leu His Met Gly Met Pro Gly Met His Gly Thr Val Ser Ala Val Gly
        275             280             285

Ala Leu Gln Arg Ser Asp Leu Leu Ile Ala Ile Gly Ser Arg Phe Asp
        290             295             300

Asp Arg Val Thr Gly Asp Val Asp Thr Phe Ala Pro Asp Ala Lys Ile
305             310             315             320

Ile His Ala Asp Ile Asp Pro Ala Glu Ile Gly Lys Ile Lys Gln Val
        325             330             335

Glu Val Pro Ile Val Gly Asp Ala Arg Glu Val Leu Ala Arg Leu Leu
        340             345             350

Glu Thr Thr Lys Ala Ser Lys Ala Glu Thr Glu Asp Ile Ser Glu Trp
        355             360             365

Val Asp Tyr Leu Lys Gly Leu Lys Ala Arg Phe Pro Arg Gly Tyr Asp
        370             375             380

Glu Gln Pro Gly Asp Leu Leu Ala Pro Gln Phe Val Ile Glu Thr Leu
385             390             395             400

Ser Lys Glu Val Gly Pro Asp Ala Ile Tyr Cys Ala Gly Val Gly Gln
        405             410             415

His Gln Met Trp Ala Ala Gln Phe Val Asp Phe Glu Lys Pro Arg Thr
        420             425             430

Trp Leu Asn Ser Gly Gly Leu Gly Thr Met Gly Tyr Ala Val Pro Ala
        435             440             445

Ala Leu Gly Ala Lys Ala Gly Ala Pro Asp Lys Glu Val Trp Ala Ile
        450             455             460

Asp Gly Asp Gly Cys Phe Gln Met Thr Asn Gln Glu Leu Thr Thr Ala
465             470             475             480

Ala Val Glu Gly Phe Pro Ile Lys Ile Ala Leu Ile Asn Asn Gly Asn
        485             490             495

Leu Gly Met Val Arg Gln Trp Gln Thr Leu Phe Tyr Glu Gly Arg Tyr
        500             505             510

Ser Asn Thr Lys Leu Arg Asn Gln Gly Glu Tyr Met Pro Asp Phe Val
        515             520             525

Thr Leu Ser Glu Gly Leu Gly Cys Val Ala Ile Arg Val Thr Lys Ala
        530             535             540

Glu Glu Val Leu Pro Ala Ile Gln Lys Ala Arg Glu Ile Asn Asp Arg
545             550             555             560

Pro Val Val Ile Asp Phe Ile Val Gly Glu Asp Ala Gln Val Trp Pro
        565             570             575

Met Val Ser Ala Gly Ser Ser Asn Ser Asp Ile Gln Tyr Ala Leu Gly
        580             585             590

Leu Arg Pro Phe Phe Asp Gly Asp Glu Ser Ala Ala Glu Asp Pro Ala
        595             600             605

Asp Ile His Glu Ala Val Ser Asp Ile Asp Ala Ala Val Glu Ser Thr
        610             615             620

Glu Ala
625
```

<210> SEQ ID NO 52
<211> LENGTH: 626
<212> TYPE: PRT
<213> ORGANISM: Artificial Sequence
<220> FEATURE:

-continued

<223> OTHER INFORMATION: acetohydroxy acid synthase variant

<400> SEQUENCE: 52

```
Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Lys Ala Ile
            20                  25                  30

Val Arg Ser Leu Glu Glu Leu Asn Ala Asp Ile Val Phe Gly Ile Pro
        35                  40                  45

Gly Gly Ala Val Leu Pro Val Tyr Asp Pro Leu Tyr Ser Ser Thr Lys
    50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Thr
            85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Pro Glu Ala Asp Ile Arg Gly Ile Thr
    130                 135                 140

Met Pro Val Thr Lys His Asn Phe Met Val Thr Asn Pro Asn Asp Ile
145                 150                 155                 160

Pro Gln Ala Leu Ala Glu Ala Phe His Leu Ala Ile Thr Gly Arg Pro
            165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ala Lys Lys Pro Val Leu Tyr Val Gly Gly Gly Val Ile Lys Ala
225                 230                 235                 240

Asp Ala His Glu Glu Leu Arg Ala Phe Ala Glu Tyr Thr Gly Ile Pro
            245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
    275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
            325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
            355                 360                 365

Val Asp Tyr Leu Lys Gly Leu Lys Ala Arg Phe Pro Arg Gly Tyr Asp
    370                 375                 380

Glu Gln Pro Gly Asp Leu Leu Ala Pro Gln Phe Val Ile Glu Thr Leu
385                 390                 395                 400
```

-continued

```
Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
            435                 440                 445

Ala Leu Gly Ala Lys Ala Gly Ala Pro Asp Lys Glu Val Trp Ala Ile
        450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
            515                 520                 525

Thr Leu Ser Glu Gly Leu Gly Cys Val Ala Ile Arg Val Thr Lys Ala
            530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
            595                 600                 605

Asp Ile His Glu Ala Val Ser Asp Ile Asp Ala Ala Val Glu Ser Thr
    610                 615                 620

Glu Ala
625

<210> SEQ ID NO 53
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 53

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Lys Ala Ile
            20                  25                  30

Val Arg Ser Leu Glu Glu Leu Asn Ala Asp Ile Val Phe Gly Ile Pro
            35                  40                  45

Gly Gly Ala Val Leu Pro Val Tyr Asp Pro Leu Tyr Ser Ser Thr Lys
        50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Thr
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
            115                 120                 125
```

-continued

Leu Leu Gly Thr Asp Ala Phe His Glu Ala Asp Ile Arg Gly Ile Thr
130             135             140

Met Pro Val Thr Lys His Asn Phe Met Val Thr Asn Pro Asn Asp Ile
145             150             155             160

Pro Gln Ala Leu Ala Glu Ala Phe His Leu Ala Ile Thr Gly Arg Pro
                165             170             175

Gly Pro Val Leu Val Asp Ile Pro Lys Asp Val Gln Asn Ala Glu Leu
                180             185             190

Asp Phe Val Trp Pro Pro Lys Ile Asp Leu Pro Gly Tyr Arg Pro Val
                195             200             205

Ser Thr Pro His Ala Arg Gln Ile Glu Gln Ala Val Lys Leu Ile Gly
    210             215             220

Glu Ala Lys Lys Pro Val Leu Tyr Val Gly Gly Gly Val Ile Lys Ala
225             230             235             240

Asp Ala His Glu Glu Leu Arg Ala Phe Ala Glu Tyr Thr Gly Ile Pro
                245             250             255

Val Val Thr Thr Leu Met Ala Leu Gly Thr Phe Pro Glu Ser His Glu
                260             265             270

Leu His Met Gly Met Pro Gly Met His Gly Thr Val Ser Ala Val Gly
    275             280             285

Ala Leu Gln Arg Ser Asp Leu Leu Ile Ala Ile Gly Ser Arg Phe Asp
    290             295             300

Asp Arg Val Thr Gly Asp Val Asp Thr Phe Ala Pro Asp Ala Lys Ile
305             310             315             320

Ile His Ala Asp Ile Asp Pro Ala Glu Ile Gly Lys Ile Lys Gln Val
                325             330             335

Glu Val Pro Ile Val Gly Asp Ala Arg Glu Val Leu Ala Arg Leu Leu
                340             345             350

Glu Thr Thr Lys Ala Ser Lys Ala Glu Thr Glu Asp Ile Ser Glu Trp
    355             360             365

Val Asp Tyr Leu Lys Gly Leu Lys Ala Arg Phe Pro Arg Gly Tyr Asp
    370             375             380

Glu Gln Pro Gly Asp Leu Leu Ala Pro Gln Phe Val Ile Glu Thr Leu
385             390             395             400

Ser Lys Glu Val Gly Pro Asp Ala Ile Tyr Cys Ala Gly Val Gly Gln
                405             410             415

His Gln Met Trp Ala Ala Gln Phe Val Asp Phe Glu Lys Pro Arg Thr
                420             425             430

Trp Leu Asn Ser Gly Gly Leu Gly Thr Met Gly Tyr Ala Val Pro Ala
    435             440             445

Ala Leu Gly Ala Lys Ala Gly Ala Pro Asp Lys Glu Val Trp Ala Ile
    450             455             460

Asp Gly Asp Gly Cys Phe Gln Met Thr Asn Gln Glu Leu Thr Thr Ala
465             470             475             480

Ala Val Glu Gly Phe Pro Ile Lys Ile Ala Leu Ile Asn Asn Gly Asn
                485             490             495

Leu Gly Met Val Arg Gln Trp Gln Thr Leu Phe Tyr Glu Gly Arg Tyr
                500             505             510

Ser Asn Thr Lys Leu Arg Asn Gln Gly Glu Tyr Met Pro Asp Phe Val
    515             520             525

Thr Leu Ser Glu Gly Leu Gly Cys Val Ala Ile Arg Val Thr Lys Ala
    530             535             540

Glu Glu Val Leu Pro Ala Ile Gln Lys Ala Arg Glu Ile Asn Asp Arg

-continued

```
545             550             555             560

Pro Val Val Ile Asp Phe Ile Val Gly Glu Asp Ala Gln Val Trp Pro
            565             570             575

Met Val Ser Ala Gly Ser Ser Asn Ser Asp Ile Gln Tyr Ala Leu Gly
            580             585             590

Leu Arg Pro Phe Phe Asp Gly Asp Glu Ser Ala Ala Glu Asp Pro Ala
            595             600             605

Asp Ile His Glu Ala Val Ser Asp Ile Asp Ala Ala Val Glu Ser Thr
    610             615             620

Glu Ala
625

<210> SEQ ID NO 54
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 54

Met Asn Val Ala Ala Ser Gln Gln Pro Thr Pro Ala Thr Val Ala Ser
1               5               10              15

Arg Gly Arg Ser Ala Ala Pro Glu Arg Met Thr Gly Ala Lys Ala Ile
            20              25              30

Val Arg Ser Leu Glu Glu Leu Asn Ala Asp Ile Val Phe Gly Ile Pro
            35              40              45

Gly Gly Ala Val Leu Pro Val Tyr Asp Pro Leu Tyr Ser Ser Thr Lys
    50              55              60

Val Arg His Val Leu Val Arg His Glu Gln Gly Ala Gly His Ala Ala
65              70              75              80

Thr Gly Tyr Ala Gln Val Thr Gly Arg Val Gly Val Cys Ile Ala Thr
            85              90              95

Ser Gly Pro Gly Ala Thr Asn Leu Val Thr Pro Ile Ala Asp Ala Asn
            100             105             110

Leu Asp Ser Val Pro Met Val Ala Ile Thr Gly Gln Val Gly Ser Gly
            115             120             125

Leu Leu Gly Thr Asp Ala Phe Leu Glu Ala Asp Ile Arg Gly Ile Thr
    130             135             140

Met Pro Val Thr Lys His Asn Phe Met Val Thr Asn Pro Asn Asp Ile
145             150             155             160

Pro Gln Ala Leu Ala Glu Ala Phe His Leu Ala Ile Thr Gly Arg Pro
            165             170             175

Gly Pro Val Leu Val Asp Ile Pro Lys Asp Val Gln Asn Ala Glu Leu
            180             185             190

Asp Phe Val Trp Pro Pro Lys Ile Asp Leu Pro Gly Tyr Arg Pro Val
            195             200             205

Ser Thr Pro His Ala Arg Gln Ile Glu Gln Ala Val Lys Leu Ile Gly
    210             215             220

Glu Ala Lys Lys Pro Val Leu Tyr Val Gly Gly Gly Val Ile Lys Ala
225             230             235             240

Asp Ala His Glu Glu Leu Arg Ala Phe Ala Glu Tyr Thr Gly Ile Pro
            245             250             255

Val Val Thr Thr Leu Met Ala Leu Gly Thr Phe Pro Glu Ser His Glu
            260             265             270

Leu His Met Gly Met Pro Gly Met His Gly Thr Val Ser Ala Val Gly
```

-continued

```
             275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
                340                 345                 350

Glu Thr Thr Lys Ala Ser Lys Ala Glu Thr Glu Asp Ile Ser Glu Trp
                355                 360                 365

Val Asp Tyr Leu Lys Gly Leu Lys Ala Arg Phe Pro Arg Gly Tyr Asp
            370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
                420                 425                 430

Trp Leu Asn Ser Gly Gly Leu Gly Thr Met Gly Tyr Ala Val Pro Ala
            435                 440                 445

Ala Leu Gly Ala Lys Ala Gly Ala Pro Asp Lys Glu Val Trp Ala Ile
    450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Trp Gln Thr Leu Phe Tyr Glu Gly Arg Tyr
                500                 505                 510

Ser Asn Thr Lys Leu Arg Asn Gln Gly Glu Tyr Met Pro Asp Phe Val
            515                 520                 525

Thr Leu Ser Glu Gly Leu Gly Cys Val Ala Ile Arg Val Thr Lys Ala
    530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
                580                 585                 590

Leu Arg Pro Phe Phe Asp Gly Asp Glu Ser Ala Ala Glu Asp Pro Ala
            595                 600                 605

Asp Ile His Glu Ala Val Ser Asp Ile Asp Ala Ala Val Glu Ser Thr
    610                 615                 620

Glu Ala
625
```

```
<210> SEQ ID NO 55
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 55

Met Asn Val Ala Ala Ser Gln Gln Pro Thr Pro Ala Thr Val Ala Ser
```

-continued

```
1              5              10             15

Arg Gly Arg Ser Ala Ala Pro Glu Arg Met Thr Gly Ala Lys Ala Ile
            20             25             30

Val Arg Ser Leu Glu Glu Leu Asn Ala Asp Ile Val Phe Gly Ile Pro
            35             40             45

Gly Gly Ala Val Leu Pro Val Tyr Asp Pro Leu Tyr Ser Ser Thr Lys
            50             55             60

Val Arg His Val Leu Val Arg His Glu Gln Gly Ala Gly His Ala Ala
65              70             75             80

Thr Gly Tyr Ala Gln Val Thr Gly Arg Val Gly Val Cys Ile Ala Thr
            85             90             95

Ser Gly Pro Gly Ala Thr Asn Leu Val Thr Pro Ile Ala Asp Ala Asn
            100            105            110

Leu Asp Ser Val Pro Met Val Ala Ile Thr Gly Gln Val Gly Ser Gly
            115            120            125

Leu Leu Gly Thr Asp Ala Phe Ile Glu Ala Asp Ile Arg Gly Ile Thr
            130            135            140

Met Pro Val Thr Lys His Asn Phe Met Val Thr Asn Pro Asn Asp Ile
145            150            155            160

Pro Gln Ala Leu Ala Glu Ala Phe His Leu Ala Ile Thr Gly Arg Pro
            165            170            175

Gly Pro Val Leu Val Asp Ile Pro Lys Asp Val Gln Asn Ala Glu Leu
            180            185            190

Asp Phe Val Trp Pro Pro Lys Ile Asp Leu Pro Gly Tyr Arg Pro Val
            195            200            205

Ser Thr Pro His Ala Arg Gln Ile Glu Gln Ala Val Lys Leu Ile Gly
            210            215            220

Glu Ala Lys Lys Pro Val Leu Tyr Val Gly Gly Gly Val Ile Lys Ala
225            230            235            240

Asp Ala His Glu Glu Leu Arg Ala Phe Ala Glu Tyr Thr Gly Ile Pro
            245            250            255

Val Val Thr Thr Leu Met Ala Leu Gly Thr Phe Pro Glu Ser His Glu
            260            265            270

Leu His Met Gly Met Pro Gly Met His Gly Thr Val Ser Ala Val Gly
            275            280            285

Ala Leu Gln Arg Ser Asp Leu Leu Ile Ala Ile Gly Ser Arg Phe Asp
            290            295            300

Asp Arg Val Thr Gly Asp Val Asp Thr Phe Ala Pro Asp Ala Lys Ile
305            310            315            320

Ile His Ala Asp Ile Asp Pro Ala Glu Ile Gly Lys Ile Lys Gln Val
            325            330            335

Glu Val Pro Ile Val Gly Asp Ala Arg Glu Val Leu Ala Arg Leu Leu
            340            345            350

Glu Thr Thr Lys Ala Ser Lys Ala Glu Thr Glu Asp Ile Ser Glu Trp
            355            360            365

Val Asp Tyr Leu Lys Gly Leu Lys Ala Arg Phe Pro Arg Gly Tyr Asp
            370            375            380

Glu Gln Pro Gly Asp Leu Leu Ala Pro Gln Phe Val Ile Glu Thr Leu
385            390            395            400

Ser Lys Glu Val Gly Pro Asp Ala Ile Tyr Cys Ala Gly Val Gly Gln
            405            410            415

His Gln Met Trp Ala Ala Gln Phe Val Asp Phe Glu Lys Pro Arg Thr
            420            425            430
```

-continued

```
Trp Leu Asn Ser Gly Gly Leu Gly Thr Met Gly Tyr Ala Val Pro Ala
        435             440             445
```

```
Ala Leu Gly Ala Lys Ala Gly Ala Pro Asp Lys Glu Val Trp Ala Ile
        450             455             460
```

```
Asp Gly Asp Gly Cys Phe Gln Met Thr Asn Gln Glu Leu Thr Thr Ala
465             470             475             480
```

```
Ala Val Glu Gly Phe Pro Ile Lys Ile Ala Leu Ile Asn Asn Gly Asn
                485             490             495
```

```
Leu Gly Met Val Arg Gln Trp Gln Thr Leu Phe Tyr Glu Gly Arg Tyr
            500             505             510
```

```
Ser Asn Thr Lys Leu Arg Asn Gln Gly Glu Tyr Met Pro Asp Phe Val
        515             520             525
```

```
Thr Leu Ser Glu Gly Leu Gly Cys Val Ala Ile Arg Val Thr Lys Ala
        530             535             540
```

```
Glu Glu Val Leu Pro Ala Ile Gln Lys Ala Arg Glu Ile Asn Asp Arg
545             550             555             560
```

```
Pro Val Val Ile Asp Phe Ile Val Gly Glu Asp Ala Gln Val Trp Pro
                565             570             575
```

```
Met Val Ser Ala Gly Ser Ser Asn Ser Asp Ile Gln Tyr Ala Leu Gly
            580             585             590
```

```
Leu Arg Pro Phe Phe Asp Gly Asp Glu Ser Ala Ala Glu Asp Pro Ala
        595             600             605
```

```
Asp Ile His Glu Ala Val Ser Asp Ile Asp Ala Ala Val Glu Ser Thr
        610             615             620
```

```
Glu Ala
625
```

```
<210> SEQ ID NO 56
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 56
```

```
Met Asn Val Ala Ala Ser Gln Gln Pro Thr Pro Ala Thr Val Ala Ser
1               5               10              15
```

```
Arg Gly Arg Ser Ala Ala Pro Glu Arg Met Thr Gly Ala Lys Ala Ile
            20              25              30
```

```
Val Arg Ser Leu Glu Glu Leu Asn Ala Asp Ile Val Phe Gly Ile Pro
        35              40              45
```

```
Gly Gly Ala Val Leu Pro Val Tyr Asp Pro Leu Tyr Ser Ser Thr Lys
        50              55              60
```

```
Val Arg His Val Leu Val Arg His Glu Gln Gly Ala Gly His Ala Ala
65              70              75              80
```

```
Thr Gly Tyr Ala Gln Val Thr Gly Arg Val Gly Val Cys Ile Ala Thr
                85              90              95
```

```
Ser Gly Pro Gly Ala Thr Asn Leu Val Thr Pro Ile Ala Asp Ala Asn
            100             105             110
```

```
Leu Asp Ser Val Pro Met Val Ala Ile Thr Gly Gln Val Gly Ser Gly
        115             120             125
```

```
Leu Leu Gly Thr Asp Ala Phe Thr Glu Ala Asp Ile Arg Gly Ile Thr
        130             135             140
```

```
Met Pro Val Thr Lys His Asn Phe Met Val Thr Asn Pro Asn Asp Ile
145             150             155             160
```

-continued

```
Pro Gln Ala Leu Ala Glu Ala Phe His Leu Ala Ile Thr Gly Arg Pro
             165                 170                 175

Gly Pro Val Leu Val Asp Ile Pro Lys Asp Val Gln Asn Ala Glu Leu
             180                 185                 190

Asp Phe Val Trp Pro Pro Lys Ile Asp Leu Pro Gly Tyr Arg Pro Val
             195                 200                 205

Ser Thr Pro His Ala Arg Gln Ile Glu Gln Ala Val Lys Leu Ile Gly
        210                 215                 220

Glu Ala Lys Lys Pro Val Leu Tyr Val Gly Gly Gly Val Ile Lys Ala
225                 230                 235                 240

Asp Ala His Glu Glu Leu Arg Ala Phe Ala Glu Tyr Thr Gly Ile Pro
             245                 250                 255

Val Val Thr Thr Leu Met Ala Leu Gly Thr Phe Pro Glu Ser His Glu
             260                 265                 270

Leu His Met Gly Met Pro Gly Met His Gly Thr Val Ser Ala Val Gly
             275                 280                 285

Ala Leu Gln Arg Ser Asp Leu Leu Ile Ala Ile Gly Ser Arg Phe Asp
        290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
             325                 330                 335

Glu Val Pro Ile Val Gly Asp Ala Arg Glu Val Leu Ala Arg Leu Leu
             340                 345                 350

Glu Thr Thr Lys Ala Ser Lys Ala Glu Thr Glu Asp Ile Ser Glu Trp
             355                 360                 365

Val Asp Tyr Leu Lys Gly Leu Lys Ala Arg Phe Pro Arg Gly Tyr Asp
        370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
             405                 410                 415

His Gln Met Trp Ala Ala Gln Phe Val Asp Phe Glu Lys Pro Arg Thr
             420                 425                 430

Trp Leu Asn Ser Gly Gly Leu Gly Thr Met Gly Tyr Ala Val Pro Ala
             435                 440                 445

Ala Leu Gly Ala Lys Ala Gly Ala Pro Asp Lys Glu Val Trp Ala Ile
        450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
             485                 490                 495

Leu Gly Met Val Arg Gln Trp Gln Thr Leu Phe Tyr Glu Gly Arg Tyr
             500                 505                 510

Ser Asn Thr Lys Leu Arg Asn Gln Gly Glu Tyr Met Pro Asp Phe Val
             515                 520                 525

Thr Leu Ser Glu Gly Leu Gly Cys Val Ala Ile Arg Val Thr Lys Ala
        530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
             565                 570                 575
```

-continued

```
Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
            595                 600                 605

Asp Ile His Glu Ala Val Ser Asp Ile Asp Ala Ala Val Glu Ser Thr
            610                 615                 620

Glu Ala
625

<210> SEQ ID NO 57
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 57

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Lys Ala Ile
            20                  25                  30

Val Arg Ser Leu Glu Glu Leu Asn Ala Asp Ile Val Phe Gly Ile Pro
            35                  40                  45

Gly Gly Ala Val Leu Pro Val Tyr Asp Pro Leu Tyr Ser Ser Thr Lys
            50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Thr
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
            115                 120                 125

Leu Leu Gly Thr Asp Ala Phe Lys Glu Ala Asp Ile Arg Gly Ile Thr
            130                 135                 140

Met Pro Val Thr Lys His Asn Phe Met Val Thr Asn Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
            195                 200                 205

Ser Thr Pro His Ala Arg Gln Ile Glu Gln Ala Val Lys Leu Ile Gly
            210                 215                 220

Glu Ala Lys Lys Pro Val Leu Tyr Val Gly Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
            275                 280                 285

Ala Leu Gln Arg Ser Asp Leu Leu Ile Ala Ile Gly Ser Arg Phe Asp
            290                 295                 300
```

```
Asp Arg Val Thr Gly Asp Val Asp Thr Phe Ala Pro Asp Ala Lys Ile
305             310             315             320

Ile His Ala Asp Ile Asp Pro Ala Glu Ile Gly Lys Ile Lys Gln Val
            325             330             335

Glu Val Pro Ile Val Gly Asp Ala Arg Glu Val Leu Ala Arg Leu Leu
            340             345             350

Glu Thr Thr Lys Ala Ser Lys Ala Glu Thr Glu Asp Ile Ser Glu Trp
            355             360             365

Val Asp Tyr Leu Lys Gly Leu Lys Ala Arg Phe Pro Arg Gly Tyr Asp
370             375             380

Glu Gln Pro Gly Asp Leu Leu Ala Pro Gln Phe Val Ile Glu Thr Leu
385             390             395             400

Ser Lys Glu Val Gly Pro Asp Ala Ile Tyr Cys Ala Gly Val Gly Gln
            405             410             415

His Gln Met Trp Ala Ala Gln Phe Val Asp Phe Glu Lys Pro Arg Thr
            420             425             430

Trp Leu Asn Ser Gly Gly Leu Gly Thr Met Gly Tyr Ala Val Pro Ala
            435             440             445

Ala Leu Gly Ala Lys Ala Gly Ala Pro Asp Lys Glu Val Trp Ala Ile
450             455             460

Asp Gly Asp Gly Cys Phe Gln Met Thr Asn Gln Glu Leu Thr Thr Ala
465             470             475             480

Ala Val Glu Gly Phe Pro Ile Lys Ile Ala Leu Ile Asn Asn Gly Asn
            485             490             495

Leu Gly Met Val Arg Gln Trp Gln Thr Leu Phe Tyr Glu Gly Arg Tyr
            500             505             510

Ser Asn Thr Lys Leu Arg Asn Gln Gly Glu Tyr Met Pro Asp Phe Val
            515             520             525

Thr Leu Ser Glu Gly Leu Gly Cys Val Ala Ile Arg Val Thr Lys Ala
            530             535             540

Glu Glu Val Leu Pro Ala Ile Gln Lys Ala Arg Glu Ile Asn Asp Arg
545             550             555             560

Pro Val Val Ile Asp Phe Ile Val Gly Glu Asp Ala Gln Val Trp Pro
            565             570             575

Met Val Ser Ala Gly Ser Ser Asn Ser Asp Ile Gln Tyr Ala Leu Gly
            580             585             590

Leu Arg Pro Phe Phe Asp Gly Asp Glu Ser Ala Ala Glu Asp Pro Ala
            595             600             605

Asp Ile His Glu Ala Val Ser Asp Ile Asp Ala Ala Val Glu Ser Thr
            610             615             620

Glu Ala
625
```

```
<210> SEQ ID NO 58
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 58

Met Asn Val Ala Ala Ser Gln Gln Pro Thr Pro Ala Thr Val Ala Ser
1               5               10              15

Arg Gly Arg Ser Ala Ala Pro Glu Arg Met Thr Gly Ala Lys Ala Ile
            20              25              30
```

-continued

```
Val Arg Ser Leu Glu Glu Leu Asn Ala Asp Ile Val Phe Gly Ile Pro
        35              40              45

Gly Gly Ala Val Leu Pro Val Tyr Asp Pro Leu Tyr Ser Ser Thr Lys
    50              55              60

Val Arg His Val Leu Val Arg His Glu Gln Gly Ala Gly His Ala Ala
65              70              75              80

Thr Gly Tyr Ala Gln Val Thr Gly Arg Val Gly Val Cys Ile Ala Thr
                85              90              95

Ser Gly Pro Gly Ala Thr Asn Leu Val Thr Pro Ile Ala Asp Ala Asn
            100             105             110

Leu Asp Ser Val Pro Met Val Ala Ile Thr Gly Gln Val Gly Ser Gly
            115             120             125

Leu Leu Gly Thr Asp Ala Phe Val Glu Ala Asp Ile Arg Gly Ile Thr
    130             135             140

Met Pro Val Thr Lys His Asn Phe Met Val Thr Asn Pro Asn Asp Ile
145             150             155             160

Pro Gln Ala Leu Ala Glu Ala Phe His Leu Ala Ile Thr Gly Arg Pro
                165             170             175

Gly Pro Val Leu Val Asp Ile Pro Lys Asp Val Gln Asn Ala Glu Leu
            180             185             190

Asp Phe Val Trp Pro Pro Lys Ile Asp Leu Pro Gly Tyr Arg Pro Val
            195             200             205

Ser Thr Pro His Ala Arg Gln Ile Glu Gln Ala Val Lys Leu Ile Gly
    210             215             220

Glu Ala Lys Lys Pro Val Leu Tyr Val Gly Gly Gly Val Ile Lys Ala
225             230             235             240

Asp Ala His Glu Glu Leu Arg Ala Phe Ala Glu Tyr Thr Gly Ile Pro
            245             250             255

Val Val Thr Thr Leu Met Ala Leu Gly Thr Phe Pro Glu Ser His Glu
            260             265             270

Leu His Met Gly Met Pro Gly Met His Gly Thr Val Ser Ala Val Gly
    275             280             285

Ala Leu Gln Arg Ser Asp Leu Leu Ile Ala Ile Gly Ser Arg Phe Asp
    290             295             300

Asp Arg Val Thr Gly Asp Val Asp Thr Phe Ala Pro Asp Ala Lys Ile
305             310             315             320

Ile His Ala Asp Ile Asp Pro Ala Glu Ile Gly Lys Ile Lys Gln Val
                325             330             335

Glu Val Pro Ile Val Gly Asp Ala Arg Glu Val Leu Ala Arg Leu Leu
            340             345             350

Glu Thr Thr Lys Ala Ser Lys Ala Glu Thr Glu Asp Ile Ser Glu Trp
            355             360             365

Val Asp Tyr Leu Lys Gly Leu Lys Ala Arg Phe Pro Arg Gly Tyr Asp
    370             375             380

Glu Gln Pro Gly Asp Leu Leu Ala Pro Gln Phe Val Ile Glu Thr Leu
385             390             395             400

Ser Lys Glu Val Gly Pro Asp Ala Ile Tyr Cys Ala Gly Val Gly Gln
                405             410             415

His Gln Met Trp Ala Ala Gln Phe Val Asp Phe Glu Lys Pro Arg Thr
            420             425             430

Trp Leu Asn Ser Gly Gly Leu Gly Thr Met Gly Tyr Ala Val Pro Ala
    435             440             445

Ala Leu Gly Ala Lys Ala Gly Ala Pro Asp Lys Glu Val Trp Ala Ile
```

-continued

```
        450             455             460

Asp Gly Asp Gly Cys Phe Gln Met Thr Asn Gln Glu Leu Thr Thr Ala
465             470             475             480

Ala Val Glu Gly Phe Pro Ile Lys Ile Ala Leu Ile Asn Asn Gly Asn
                485             490             495

Leu Gly Met Val Arg Gln Trp Gln Thr Leu Phe Tyr Glu Gly Arg Tyr
                500             505             510

Ser Asn Thr Lys Leu Arg Asn Gln Gly Glu Tyr Met Pro Asp Phe Val
            515             520             525

Thr Leu Ser Glu Gly Leu Gly Cys Val Ala Ile Arg Val Thr Lys Ala
            530             535             540

Glu Glu Val Leu Pro Ala Ile Gln Lys Ala Arg Glu Ile Asn Asp Arg
545             550             555             560

Pro Val Val Ile Asp Phe Ile Val Gly Glu Asp Ala Gln Val Trp Pro
                565             570             575

Met Val Ser Ala Gly Ser Ser Asn Ser Asp Ile Gln Tyr Ala Leu Gly
                580             585             590

Leu Arg Pro Phe Phe Asp Gly Asp Glu Ser Ala Ala Glu Asp Pro Ala
            595             600             605

Asp Ile His Glu Ala Val Ser Asp Ile Asp Ala Ala Val Glu Ser Thr
            610             615             620

Glu Ala
625

<210> SEQ ID NO 59
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 59

Met Asn Val Ala Ala Ser Gln Gln Pro Thr Pro Ala Thr Val Ala Ser
1               5               10              15

Arg Gly Arg Ser Ala Ala Pro Glu Arg Met Thr Gly Ala Lys Ala Ile
                20              25              30

Val Arg Ser Leu Glu Glu Leu Asn Ala Asp Ile Val Phe Gly Ile Pro
            35              40              45

Gly Gly Ala Val Leu Pro Val Tyr Asp Pro Leu Tyr Ser Ser Thr Lys
        50              55              60

Val Arg His Val Leu Val Arg His Glu Gln Gly Ala Gly His Ala Ala
65              70              75              80

Thr Gly Tyr Ala Gln Val Thr Gly Arg Val Gly Val Cys Ile Ala Thr
                85              90              95

Ser Gly Pro Gly Ala Thr Asn Leu Val Thr Pro Ile Ala Asp Ala Asn
                100             105             110

Leu Asp Ser Val Pro Met Val Ala Ile Thr Gly Gln Val Gly Ser Gly
            115             120             125

Leu Leu Gly Thr Asp Ala Phe Ala Glu Ala Asp Ile Arg Gly Ile Thr
            130             135             140

Met Pro Val Thr Lys His Asn Phe Met Val Thr Asn Pro Asn Asp Ile
145             150             155             160

Pro Gln Ala Leu Ala Glu Ala Phe His Leu Ala Ile Thr Gly Arg Pro
                165             170             175

Gly Pro Val Leu Val Asp Ile Pro Lys Asp Val Gln Asn Ala Glu Leu
```

```
            180                 185                 190

Asp Phe Val Trp Pro Pro Lys Ile Asp Leu Pro Gly Tyr Arg Pro Val
            195                 200                 205

Ser Thr Pro His Ala Arg Gln Ile Glu Gln Ala Val Lys Leu Ile Gly
            210                 215                 220

Glu Ala Lys Lys Pro Val Leu Tyr Val Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
                260                 265                 270

Leu His Met Gly Met Pro Gly Met His Gly Thr Val Ser Ala Val Gly
            275                 280                 285

Ala Leu Gln Arg Ser Asp Leu Leu Ile Ala Ile Gly Ser Arg Phe Asp
            290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
            355                 360                 365

Val Asp Tyr Leu Lys Gly Leu Lys Ala Arg Phe Pro Arg Gly Tyr Asp
        370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
            435                 440                 445

Ala Leu Gly Ala Lys Ala Gly Ala Pro Asp Lys Glu Val Trp Ala Ile
        450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
            515                 520                 525

Thr Leu Ser Glu Gly Leu Gly Cys Val Ala Ile Arg Val Thr Lys Ala
        530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
            595                 600                 605
```

-continued

```
Asp Ile His Glu Ala Val Ser Asp Ile Asp Ala Ala Val Glu Ser Thr
    610             615             620

Glu Ala
625

<210> SEQ ID NO 60
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 60

Met Asn Val Ala Ala Ser Gln Gln Pro Thr Pro Ala Thr Val Ala Ser
1               5               10              15

Arg Gly Arg Ser Ala Ala Pro Glu Arg Met Thr Gly Ala Lys Ala Ile
            20              25              30

Val Arg Ser Leu Glu Glu Leu Asn Ala Asp Ile Val Phe Gly Ile Pro
        35              40              45

Gly Gly Ala Val Leu Pro Val Tyr Asp Pro Leu Tyr Ser Ser Thr Lys
    50              55              60

Val Arg His Val Leu Val Arg His Glu Gln Gly Ala Gly His Ala Ala
65              70              75              80

Thr Gly Tyr Ala Gln Val Thr Gly Arg Val Gly Val Cys Ile Ala Thr
            85              90              95

Ser Gly Pro Gly Ala Thr Asn Leu Val Thr Pro Ile Ala Asp Ala Asn
            100             105             110

Leu Asp Ser Val Pro Met Val Ala Ile Thr Gly Gln Val Gly Ser Gly
        115             120             125

Leu Leu Gly Thr Asp Ala Phe Asp Glu Ala Asp Ile Arg Gly Ile Thr
    130             135             140

Met Pro Val Thr Lys His Asn Phe Met Val Thr Asn Pro Asn Asp Ile
145             150             155             160

Pro Gln Ala Leu Ala Glu Ala Phe His Leu Ala Ile Thr Gly Arg Pro
            165             170             175

Gly Pro Val Leu Val Asp Ile Pro Lys Asp Val Gln Asn Ala Glu Leu
            180             185             190

Asp Phe Val Trp Pro Pro Lys Ile Asp Leu Pro Gly Tyr Arg Pro Val
        195             200             205

Ser Thr Pro His Ala Arg Gln Ile Glu Gln Ala Val Lys Leu Ile Gly
    210             215             220

Glu Ala Lys Lys Pro Val Leu Tyr Val Gly Gly Gly Val Ile Lys Ala
225             230             235             240

Asp Ala His Glu Glu Leu Arg Ala Phe Ala Glu Tyr Thr Gly Ile Pro
            245             250             255

Val Val Thr Thr Leu Met Ala Leu Gly Thr Phe Pro Glu Ser His Glu
            260             265             270

Leu His Met Gly Met Pro Gly Met His Gly Thr Val Ser Ala Val Gly
        275             280             285

Ala Leu Gln Arg Ser Asp Leu Leu Ile Ala Ile Gly Ser Arg Phe Asp
    290             295             300

Asp Arg Val Thr Gly Asp Val Asp Thr Phe Ala Pro Asp Ala Lys Ile
305             310             315             320

Ile His Ala Asp Ile Asp Pro Ala Glu Ile Gly Lys Ile Lys Gln Val
            325             330             335
```

-continued

```
Glu Val Pro Ile Val Gly Asp Ala Arg Glu Val Leu Ala Arg Leu Leu
        340             345             350

Glu Thr Thr Lys Ala Ser Lys Ala Glu Thr Glu Asp Ile Ser Glu Trp
        355             360             365

Val Asp Tyr Leu Lys Gly Leu Lys Ala Arg Phe Pro Arg Gly Tyr Asp
        370             375             380

Glu Gln Pro Gly Asp Leu Leu Ala Pro Gln Phe Val Ile Glu Thr Leu
385             390             395             400

Ser Lys Glu Val Gly Pro Asp Ala Ile Tyr Cys Ala Gly Val Gly Gln
        405             410             415

His Gln Met Trp Ala Ala Gln Phe Val Asp Phe Glu Lys Pro Arg Thr
        420             425             430

Trp Leu Asn Ser Gly Gly Leu Gly Thr Met Gly Tyr Ala Val Pro Ala
        435             440             445

Ala Leu Gly Ala Lys Ala Gly Ala Pro Asp Lys Glu Val Trp Ala Ile
        450             455             460

Asp Gly Asp Gly Cys Phe Gln Met Thr Asn Gln Glu Leu Thr Thr Ala
465             470             475             480

Ala Val Glu Gly Phe Pro Ile Lys Ile Ala Leu Ile Asn Asn Gly Asn
        485             490             495

Leu Gly Met Val Arg Gln Trp Gln Thr Leu Phe Tyr Glu Gly Arg Tyr
        500             505             510

Ser Asn Thr Lys Leu Arg Asn Gln Gly Glu Tyr Met Pro Asp Phe Val
        515             520             525

Thr Leu Ser Glu Gly Leu Gly Cys Val Ala Ile Arg Val Thr Lys Ala
        530             535             540

Glu Glu Val Leu Pro Ala Ile Gln Lys Ala Arg Glu Ile Asn Asp Arg
545             550             555             560

Pro Val Val Ile Asp Phe Ile Val Gly Glu Asp Ala Gln Val Trp Pro
        565             570             575

Met Val Ser Ala Gly Ser Ser Asn Ser Asp Ile Gln Tyr Ala Leu Gly
        580             585             590

Leu Arg Pro Phe Phe Asp Gly Asp Glu Ser Ala Ala Glu Asp Pro Ala
        595             600             605

Asp Ile His Glu Ala Val Ser Asp Ile Asp Ala Ala Val Glu Ser Thr
        610             615             620

Glu Ala
625
```

```
<210> SEQ ID NO 61
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 61

Met Asn Val Ala Ala Ser Gln Gln Pro Thr Pro Ala Thr Val Ala Ser
1               5               10              15

Arg Gly Arg Ser Ala Ala Pro Glu Arg Met Thr Gly Ala Lys Ala Ile
        20              25              30

Val Arg Ser Leu Glu Glu Leu Asn Ala Asp Ile Val Phe Gly Ile Pro
        35              40              45

Gly Gly Ala Val Leu Pro Val Tyr Asp Pro Leu Tyr Ser Ser Thr Lys
        50              55              60
```

-continued

```
Val Arg His Val Leu Val Arg His Glu Gln Gly Ala Gly His Ala Ala
65              70              75              80

Thr Gly Tyr Ala Gln Val Thr Gly Arg Val Gly Val Cys Ile Ala Thr
            85              90              95

Ser Gly Pro Gly Ala Thr Asn Leu Val Thr Pro Ile Ala Asp Ala Asn
            100             105             110

Leu Asp Ser Val Pro Met Val Ala Ile Thr Gly Gln Val Gly Ser Gly
            115             120             125

Leu Leu Gly Thr Asp Ala Phe Glu Glu Ala Asp Ile Arg Gly Ile Thr
    130             135             140

Met Pro Val Thr Lys His Asn Phe Met Val Thr Asn Pro Asn Asp Ile
145             150             155             160

Pro Gln Ala Leu Ala Glu Ala Phe His Leu Ala Ile Thr Gly Arg Pro
            165             170             175

Gly Pro Val Leu Val Asp Ile Pro Lys Asp Val Gln Asn Ala Glu Leu
            180             185             190

Asp Phe Val Trp Pro Pro Lys Ile Asp Leu Pro Gly Tyr Arg Pro Val
            195             200             205

Ser Thr Pro His Ala Arg Gln Ile Glu Gln Ala Val Lys Leu Ile Gly
    210             215             220

Glu Ala Lys Lys Pro Val Leu Tyr Val Gly Gly Gly Val Ile Lys Ala
225             230             235             240

Asp Ala His Glu Glu Leu Arg Ala Phe Ala Glu Tyr Thr Gly Ile Pro
            245             250             255

Val Val Thr Thr Leu Met Ala Leu Gly Thr Phe Pro Glu Ser His Glu
            260             265             270

Leu His Met Gly Met Pro Gly Met His Gly Thr Val Ser Ala Val Gly
    275             280             285

Ala Leu Gln Arg Ser Asp Leu Leu Ile Ala Ile Gly Ser Arg Phe Asp
    290             295             300

Asp Arg Val Thr Gly Asp Val Asp Thr Phe Ala Pro Asp Ala Lys Ile
305             310             315             320

Ile His Ala Asp Ile Asp Pro Ala Glu Ile Gly Lys Ile Lys Gln Val
            325             330             335

Glu Val Pro Ile Val Gly Asp Ala Arg Glu Val Leu Ala Arg Leu Leu
            340             345             350

Glu Thr Thr Lys Ala Ser Lys Ala Glu Thr Glu Asp Ile Ser Glu Trp
    355             360             365

Val Asp Tyr Leu Lys Gly Leu Lys Ala Arg Phe Pro Arg Gly Tyr Asp
    370             375             380

Glu Gln Pro Gly Asp Leu Leu Ala Pro Gln Phe Val Ile Glu Thr Leu
385             390             395             400

Ser Lys Glu Val Gly Pro Asp Ala Ile Tyr Cys Ala Gly Val Gly Gln
            405             410             415

His Gln Met Trp Ala Ala Gln Phe Val Asp Phe Glu Lys Pro Arg Thr
            420             425             430

Trp Leu Asn Ser Gly Gly Leu Gly Thr Met Gly Tyr Ala Val Pro Ala
            435             440             445

Ala Leu Gly Ala Lys Ala Gly Ala Pro Asp Lys Glu Val Trp Ala Ile
    450             455             460

Asp Gly Asp Gly Cys Phe Gln Met Thr Asn Gln Glu Leu Thr Thr Ala
465             470             475             480
```

-continued

```
Ala Val Glu Gly Phe Pro Ile Lys Ile Ala Leu Ile Asn Asn Gly Asn
                485             490             495

Leu Gly Met Val Arg Gln Trp Gln Thr Leu Phe Tyr Glu Gly Arg Tyr
            500             505             510

Ser Asn Thr Lys Leu Arg Asn Gln Gly Glu Tyr Met Pro Asp Phe Val
            515             520             525

Thr Leu Ser Glu Gly Leu Gly Cys Val Ala Ile Arg Val Thr Lys Ala
        530             535             540

Glu Glu Val Leu Pro Ala Ile Gln Lys Ala Arg Glu Ile Asn Asp Arg
545             550             555             560

Pro Val Val Ile Asp Phe Ile Val Gly Glu Asp Ala Gln Val Trp Pro
                565             570             575

Met Val Ser Ala Gly Ser Ser Asn Ser Asp Ile Gln Tyr Ala Leu Gly
            580             585             590

Leu Arg Pro Phe Phe Asp Gly Asp Glu Ser Ala Ala Glu Asp Pro Ala
            595             600             605

Asp Ile His Glu Ala Val Ser Asp Ile Asp Ala Ala Val Glu Ser Thr
        610             615             620

Glu Ala
625

<210> SEQ ID NO 62
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 62

Met Asn Val Ala Ala Ser Gln Gln Pro Thr Pro Ala Thr Val Ala Ser
1               5               10              15

Arg Gly Arg Ser Ala Ala Pro Glu Arg Met Thr Gly Ala Lys Ala Ile
            20              25              30

Val Arg Ser Leu Glu Glu Leu Asn Ala Asp Ile Val Phe Gly Ile Pro
            35              40              45

Gly Gly Ala Val Leu Pro Val Tyr Asp Pro Leu Tyr Ser Ser Thr Lys
        50              55              60

Val Arg His Val Leu Val Arg His Glu Gln Gly Ala Gly His Ala Ala
65              70              75              80

Thr Gly Tyr Ala Gln Val Thr Gly Arg Val Gly Val Cys Ile Ala Thr
                85              90              95

Ser Gly Pro Gly Ala Thr Asn Leu Val Thr Pro Ile Ala Asp Ala Asn
            100             105             110

Leu Asp Ser Val Pro Met Val Ala Ile Thr Gly Gln Val Gly Ser Gly
            115             120             125

Leu Leu Gly Thr Asp Ala Phe Gly Glu Ala Asp Ile Arg Gly Ile Thr
        130             135             140

Met Pro Val Thr Lys His Asn Phe Met Val Thr Asn Pro Asn Asp Ile
145             150             155             160

Pro Gln Ala Leu Ala Glu Ala Phe His Leu Ala Ile Thr Gly Arg Pro
                165             170             175

Gly Pro Val Leu Val Asp Ile Pro Lys Asp Val Gln Asn Ala Glu Leu
            180             185             190

Asp Phe Val Trp Pro Pro Lys Ile Asp Leu Pro Gly Tyr Arg Pro Val
            195             200             205
```

-continued

```
Ser Thr Pro His Ala Arg Gln Ile Glu Gln Ala Val Lys Leu Ile Gly
    210                 215                 220

Glu Ala Lys Lys Pro Val Leu Tyr Val Gly Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
                260                 265                 270

Leu His Met Gly Met Pro Gly Met His Gly Thr Val Ser Ala Val Gly
            275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
            355                 360                 365

Val Asp Tyr Leu Lys Gly Leu Lys Ala Arg Phe Pro Arg Gly Tyr Asp
    370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
            435                 440                 445

Ala Leu Gly Ala Lys Ala Gly Ala Pro Asp Lys Glu Val Trp Ala Ile
    450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
            515                 520                 525

Thr Leu Ser Glu Gly Leu Gly Cys Val Ala Ile Arg Val Thr Lys Ala
    530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
            595                 600                 605

Asp Ile His Glu Ala Val Ser Asp Ile Asp Ala Ala Val Glu Ser Thr
    610                 615                 620

Glu Ala
```

-continued

625

```
<210> SEQ ID NO 63
<211> LENGTH: 626
<212> TYPE: PRT
<213> ORGANISM: Artificial Sequence
<220> FEATURE:
<223> OTHER INFORMATION: acetohydroxy acid synthase variant

<400> SEQUENCE: 63

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Lys Ala Ile
            20                  25                  30

Val Arg Ser Leu Glu Glu Leu Asn Ala Asp Ile Val Phe Gly Ile Pro
        35                  40                  45

Gly Gly Ala Val Leu Pro Val Tyr Asp Pro Leu Tyr Ser Ser Thr Lys
    50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Thr
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Trp Glu Ala Asp Ile Arg Gly Ile Thr
    130                 135                 140

Met Pro Val Thr Lys His Asn Phe Met Val Thr Asn Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ala Lys Lys Pro Val Leu Tyr Val Gly Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
        275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
```

-continued

```
          355                    360                    365
Val Asp Tyr Leu Lys Gly Leu Lys Ala Arg Phe Pro Arg Gly Tyr Asp
    370                    375                    380

Glu Gln Pro Gly Asp Leu Leu Ala Pro Gln Phe Val Ile Glu Thr Leu
385                    390                    395                    400

Ser Lys Glu Val Gly Pro Asp Ala Ile Tyr Cys Ala Gly Val Gly Gln
                   405                    410                    415

His Gln Met Trp Ala Ala Gln Phe Val Asp Phe Glu Lys Pro Arg Thr
                   420                    425                    430

Trp Leu Asn Ser Gly Gly Leu Gly Thr Met Gly Tyr Ala Val Pro Ala
                   435                    440                    445

Ala Leu Gly Ala Lys Ala Gly Ala Pro Asp Lys Glu Val Trp Ala Ile
    450                    455                    460

Asp Gly Asp Gly Cys Phe Gln Met Thr Asn Gln Glu Leu Thr Thr Ala
465                    470                    475                    480

Ala Val Glu Gly Phe Pro Ile Lys Ile Ala Leu Ile Asn Asn Gly Asn
                   485                    490                    495

Leu Gly Met Val Arg Gln Trp Gln Thr Leu Phe Tyr Glu Gly Arg Tyr
                   500                    505                    510

Ser Asn Thr Lys Leu Arg Asn Gln Gly Glu Tyr Met Pro Asp Phe Val
                   515                    520                    525

Thr Leu Ser Glu Gly Leu Gly Cys Val Ala Ile Arg Val Thr Lys Ala
                   530                    535                    540

Glu Glu Val Leu Pro Ala Ile Gln Lys Ala Arg Glu Ile Asn Asp Arg
545                    550                    555                    560

Pro Val Val Ile Asp Phe Ile Val Gly Glu Asp Ala Gln Val Trp Pro
                   565                    570                    575

Met Val Ser Ala Gly Ser Ser Asn Ser Asp Ile Gln Tyr Ala Leu Gly
                   580                    585                    590

Leu Arg Pro Phe Phe Asp Gly Asp Glu Ser Ala Ala Glu Asp Pro Ala
                   595                    600                    605

Asp Ile His Glu Ala Val Ser Asp Ile Asp Ala Ala Val Glu Ser Thr
    610                    615                    620

Glu Ala
625
```

<210> SEQ ID NO 64
<211> LENGTH: 38
<212> TYPE: DNA
<213> ORGANISM: Artificial Sequence
<220> FEATURE:
<223> OTHER INFORMATION: primer

<400> SEQUENCE: 64
tcgagctcgg tacccgctca ctgaggacgc ttttgcac                                    38

<210> SEQ ID NO 65
<211> LENGTH: 24
<212> TYPE: DNA
<213> ORGANISM: Artificial Sequence
<220> FEATURE:
<223> OTHER INFORMATION: primer

<400> SEQUENCE: 65
gaagagcgcg atgatgatgc acac                                                   24

<210> SEQ ID NO 66

```
<211> LENGTH: 23
<212> TYPE: DNA
<213> ORGANISM: Artificial Sequence
<220> FEATURE:
<223> OTHER INFORMATION: primer

<400> SEQUENCE: 66
tgatgatgca cacctgatcg tgg                                             23

<210> SEQ ID NO 67
<211> LENGTH: 38
<212> TYPE: DNA
<213> ORGANISM: Artificial Sequence
<220> FEATURE:
<223> OTHER INFORMATION: primer

<400> SEQUENCE: 67
ggggatcctc tagaggacaa ggttttggaa gatgctcg                             38

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
agcgcgatga tgatgcacac                                                 20

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
catctggctt ggaagtggaa                                                 20

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
atgacctcag catctgcccc                                                 20

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
tccgcctcga aagggactaa                                                 20

<210> SEQ ID NO 72
<211> LENGTH: 35
<212> TYPE: DNA
<213> ORGANISM: Artificial Sequence
<220> FEATURE:
<223> OTHER INFORMATION: primer

<400> SEQUENCE: 72
```

-continued

```
tcgagctcgg tacccatgag tgaaacatac gtgtc                               35

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
ggtactctga cagcgtgatg                                               20

<210> SEQ ID NO 74
<211> LENGTH: 22
<212> TYPE: DNA
<213> ORGANISM: Artificial Sequence
<220> FEATURE:
<223> OTHER INFORMATION: primer

<400> SEQUENCE: 74
cacgctggca gagtacctca ag                                            22

<210> SEQ ID NO 75
<211> LENGTH: 35
<212> TYPE: DNA
<213> ORGANISM: Artificial Sequence
<220> FEATURE:
<223> OTHER INFORMATION: primer

<400> SEQUENCE: 75
ggggatcctc tagagtggat gcacagtggg ttgac                              35

<210> SEQ ID NO 76
<211> LENGTH: 24
<212> TYPE: DNA
<213> ORGANISM: Artificial Sequence
<220> FEATURE:
<223> OTHER INFORMATION: primer

<400> SEQUENCE: 76
gtaacgaact tggggtcatt gagt                                          24

<210> SEQ ID NO 77
<211> LENGTH: 22
<212> TYPE: DNA
<213> ORGANISM: Artificial Sequence
<220> FEATURE:
<223> OTHER INFORMATION: primer

<400> SEQUENCE: 77
atgagtgaaa catacgtgtc tg                                            22

<210> SEQ ID NO 78
<211> LENGTH: 23
<212> TYPE: DNA
<213> ORGANISM: Artificial Sequence
<220> FEATURE:
<223> OTHER INFORMATION: primer

<400> SEQUENCE: 78
ttaggtcaag tattcgtact cag                                           23
```

ACETOHYDROXY ACID SYNTHASE VARIANT AND MICROORGANISM INCLUDING THE SAME

A computer readable text file, entitled "SequenceListing.txt," created on May 26, 2022 with a file size of 119,440 bytes contains the sequence listing for this application and is hereby incorporated by reference in its entirety.

TECHNICAL FIELD

The present disclosure relates to a novel variant of acetohydroxy acid synthase protein, a polynucleotide encoding the variant, a microorganism including the variant, and a method of producing L-isoleucine using the microorganism.

BACKGROUND ART

Branched-chain amino acids, i.e., L-valine, L-leucine, and L-isoleucine, are known to increase protein levels in an individual and play an important role as an energy source during exercise, and thus are widely used in medical products, foods, etc.

As representative microorganisms producing branched-chain amino acids, *Corynebacterium glutamicum* and *Escherichia coli* are used. In these microorganisms, L-isoleucine among branched-chain amino acids shares its main biosynthesis pathways with the other branched-chain amino acids such as L-valine or L-leucine. With regard to L-isoleucine biosynthesis pathways, pyruvate produced during glycolysis and 2-ketobutyrate produced from L-threonine, which is an aspartate (aspartic acid)-derived amino acid, are used as precursors. From the two precursors, 2-aceto-2-hydroxyacetate is synthesized by the enzymatic action of acetohydroxy acid synthase (AHAS), and subsequently, 2,3-dihydroxy-3-methylvalerate is produced by acetohydroxy acid isomeroreductase, and 2-keto-3-methylvalerate is produced by dihydroxy acid dehydratase. Finally, L-isoleucine is produced by the action of aminotransferase. Further, the acetohydroxy acid synthase catalyzes decarboxylation of pyruvate and a condensation reaction with another pyruvate molecule to produce acetolactate, which is a precursor of valine and leucine.

Among the branched-chain amino acids sharing biosynthesis pathways, L-isoleucine and L-valine have very similar chemical structures and properties, and by-products such as norvaline and alpha-amino butyric acid (AABA) also share biosynthetic pathways with L-isoleucine. Therefore, when production of L-isoleucine is increased, by-products are also produced in a large amount. For this reason, to produce L-isoleucine in a high yield and with high purity, high purification costs are required, and thus it is necessary to develop a strain having the increased ability to produce a target product while reducing production of by-products as much as possible.

Acetohydroxy acid synthase (AHAS) is an enzyme that plays an important role in biosynthesis pathways of branched-chain amino acids, and is encoded by ilvBN, ilvGM, or ilvIH gene according to the kind of microorganisms. In the case of *Corynebacterium glutamicum*, AHAS is encoded by ilvBN gene. ilvBN gene undergoes feedback inhibition by the final product L-isoleucine among the branched-chain amino acids so that expression of the gene and activity of the enzyme are inhibited. Thus, it is very important to optimize expression of the gene and regulate activity of the enzyme for producing high-yield L-isoleucine-producing strains. However, previous studies thereon were mainly focused on release of feedback inhibition due to modifications of acetohydroxy acid synthase small subunit (IlvN protein) (Protein Expr Purif. 2015 May; 109:106-12., US 2014-0335574, US 2009-496475, US 2006-303888, US 2008-245610), thus revealing a serious lack of relevant studies.

In view of this technical background, the present inventors have made extensive efforts to develop a microorganism having an enhanced ability to produce L-isoleucine, and as a result, they have developed a variant of acetohydroxy acid synthase, specifically, a large subunit (ilvB) variant. Accordingly, the present inventors confirmed high production of L-isoleucine in a microorganism including the variant, thereby completing the present disclosure.

DISCLOSURE

Technical Problem

An object of the present disclosure is to provide a protein variant having acetohydroxy acid synthase activity, wherein glutamine, which is an amino acid at position 136 in an amino acid sequence of SEQ ID NO: 1, is substituted with an amino acid other than glutamine.

Another object of the present disclosure is to provide a polynucleotide encoding the protein variant, and a vector including the same.

Still another object of the present disclosure is to provide a microorganism producing L-isoleucine, which includes the protein variant.

Still another object of the present disclosure is to provide a method of producing L-isoleucine, the method including culturing the microorganism producing L-isoleucine in a medium.

Technical Solution

The present disclosure will be described in more detail.

Meanwhile, each description and embodiment disclosed in the present disclosure may also be applied to other descriptions and embodiments. That is, all combinations of various elements disclosed in the present disclosure fall within the scope of the present disclosure. Further, the scope of the present disclosure is not limited by the specific description below.

Further, those skilled in the art will recognize or be able to ascertain, using no more than routine experimentation, many equivalents to the specific embodiments of the present disclosure described herein. Further, these equivalents should be interpreted to fall within the present disclosure.

One aspect of the present disclosure provides a protein variant having acetohydroxy acid synthase activity, wherein glutamine, which is an amino acid at position 136 in an amino acid sequence of SEQ ID NO: 1, is substituted with an amino acid other than glutamine. The protein variant having acetohydroxy acid synthase activity may be used interchangeably with a variant protein, a modified protein, an acetohydroxy acid synthase variant, a variant acetohydroxy acid synthase, a modified acetohydroxy acid synthase, etc.

Specifically, the polypeptide may be a protein variant having acetohydroxy acid synthase (AHAS) activity, wherein glutamine, which is an amino acid at position 136 in the amino acid sequence of SEQ ID NO: 1, is substituted with asparagine, arginine, phenylalanine, serine, tyrosine, methionine, cysteine, proline, histidine, leucine, isoleucine, threonine, lysine, valine, alanine, aspartic acid, glutamic acid, glycine, or tryptophan, but is not limited thereto.

As used herein, the term "acetohydroxy acid synthase (AHAS)" refers to an enzyme involved in the biosynthesis of branched-chain amino acids, and it may be involved in the first step of the biosynthesis of branched-chain amino acids. Specifically, acetohydroxy acid synthase may catalyze decarboxylation of pyruvate and a condensation reaction with another pyruvate molecule to produce acetolactate, which is a precursor of valine, or may catalyze decarboxylation of pyruvate and a condensation reaction with 2-keto-butyrate to produce acetohydroxybutyrate, which is a precursor of isoleucine. Starting from the produced acetohydroxybutyrate, L-isoleucine may be biosynthesized through sequential reactions catalyzed by acetohydroxy acid isomeroreductase, dihydroxy acid dehydratase, and transaminase B.

Accordingly, the acetohydroxy acid synthase is an important enzyme in the biosynthesis pathways of branched-chain amino acids. Acetohydroxy acid synthase is encoded by two genes, i.e., ilvB and ilvN. The ilvB gene encodes the large subunit of acetohydroxy acid synthase (IlvB), and the ilvN gene encodes the small subunit of acetohydroxy acid synthase (IlvN).

As used herein, the term "branched-chain amino acid" refers to an amino acid with a branched alkyl group on the side chain, and it includes valine, leucine, and isoleucine. Specifically, in the present disclosure, the branched-chain amino acid may be L-isoleucine, L-valine, or L-leucine, but is not limited thereto.

In the present disclosure, the acetohydroxy acid synthase may be derived from a microorganism of the genus *Corynebacterium*, and specifically, from *Corynebacterium glutamicum*. The large subunit ilvB protein of acetohydroxy acid synthase derived from *Corynebacterium glutamicum* may be, for example, a protein including the amino acid sequence of SEQ ID NO: 1. The protein including the amino acid sequence of SEQ ID NO: 1 may be used interchangeably with a protein having the amino acid sequence of SEQ ID NO: 1 or a protein consisting of the amino acid sequence of SEQ ID NO: 1.

Further, although the large subunit ilvB protein of acetohydroxy acid synthase in the present disclosure is defined as the protein including the amino acid sequence of SEQ ID NO: 1, it does not exclude a mutation that may occur by adding a meaningless sequence upstream or downstream of the amino acid sequence of SEQ ID NO: 1, a naturally occurring mutation, or a silent mutation, and it is apparent to those skilled in the art that as long as a protein has activity identical or corresponding to that of the protein including the amino acid sequence of SEQ ID NO: 1, it corresponds to the large subunit ilvB protein of acetohydroxy acid synthase of the present disclosure. As a specific example, the large subunit ilvB protein of acetohydroxy acid synthase of the present disclosure may be a protein consisting of the amino acid sequence of SEQ ID NO: 1, or a protein consisting of an amino acid sequence having 80%, 90%, 95%, 97%, or 99% or more homology or identity thereto. Additionally, it is obvious that any protein having an amino acid sequence with deletion, modification, substitution, or addition in part of the sequence may also be included within the scope of the protein to be mutated in the present disclosure, as long as the amino acid sequence has a homology or identity described above and exhibits efficacy corresponding to that of the protein.

In other words, although described as "a protein or polypeptide having an amino acid sequence of a specific SEQ ID NO" or "a protein or polypeptide consisting of an amino acid sequence of a specific SEQ ID NO" in the present disclosure, it is obvious that any protein having an amino acid sequence with deletion, modification, substitution, or addition in part of the sequence may also be used in the present disclosure, as long as the protein may have an activity identical or corresponding to that of a poly peptide consisting of the amino acid sequence of the corresponding SEQ ID NO. For example, it is obvious that any polypeptide may belong to the "polypeptide consisting of the amino acid sequence of SEQ ID NO: t", as long as it has an activity identical or corresponding to that of the "polypeptide consisting of the amino acid sequence of SEQ ID NO: 1".

The protein variant having acetohydroxy acid synthase activity provided in the present disclosure may refer to a variant for which acetohydroxy acid synthase activity exceeds 100% by substituting an amino acid at a specific position in the protein having acetohydroxy acid synthase activity described above, as compared with the protein before modification, or a variant for which feedback inhibition by L-isoleucine or an analog thereof is released.

As used herein, the term "variant" refers to a protein, of which one or more amino acids differ from the recited sequence in conservative substitutions and/or modifications, but it retains functions or properties of the protein. Variants differ from an identified sequence by substitution, deletion, or addition of several amino acids. Such variants may be generally identified by modifying one or more amino acids in the amino acid sequence of the protein and evaluating the properties of the modified protein.

In other words, an ability of a variant may be increased, unchanged, or decreased, as compared with that of a native protein. Other variants may include variants in which a portion has been removed from the N- and/or C-terminus of a mature protein. The term "variant" may be used interchangeably with terms such as modification, modified protein, modified polypeptide, mutant, mutein, divergent, variant, etc., and the term is not limited as long as it is used with a meaning of modification. With respect to the object of the present disclosure, the variant may be a variant in which the activity of the protein is increased or feedback inhibition is released, as compared with a natural wild-type or non-modified protein, but is not limited thereto.

As used herein, the term "conservative substitution" means substitution of one amino acid with another amino acid that has similar structural and/or chemical properties. Such amino acid substitutions may be generally made on the basis of similarity in polarity, charge (basic/acidic), solubility, hydrophobicity, hydrophilicity, and/or the amphipathic nature of residues.

Further, variants may include deletion or addition of amino acids that have minimal influence on properties and a secondary structure of the polypeptide. For example, a polypeptide may be conjugated to a signal (or leader) sequence at the N-terminus of the protein, which co-translationally or post-translationally directs transfer of the protein. In addition, the polypeptide may also be conjugated to another sequence or a linker for identification, purification, or synthesis of the polypeptide.

The "substitution with another amino acid" is not limited, as long as another amino acid is an amino acid different from the amino acid before substitution. That is, the substitution is not limited, as long as glutamine, which is an amino acid at position 136 from the N-terminus of the amino acid sequence of SEQ ID NO: 1, is substituted with an amino acid residue other than glutamine. Meanwhile, in the present disclosure, when the term "a specific amino acid is substituted" is used, it is obvious that the amino acid is substituted with an amino acid different from the amino acid before the substitution, even if it is not separately indicated that the amino acid is substituted with another amino acid.

Alternatively, the protein variant may be a variant in which the amino acid at position 136 from the N-terminus of the amino acid sequence of SEQ ID NO: 1 is substituted with asparagine, arginine, phenylalanine, serine, tyrosine, methionine, cysteine, proline, histidine, leucine, isoleucine, threonine, lysine, valine, alanine, aspartic acid, glutamic acid, glycine, or tryptophan, but is not limited thereto.

As described, the protein variant of the present disclosure has the enhanced acetohydroxy acid synthase activity, as compared with that of the protein before modification.

It is apparent that the protein variant of the present disclosure, in which the amino acid at position 136 from the N-terminus of the sequence of SEQ ID NO: 1 is substituted with another amino acid, includes a protein variant in which an amino acid at a position corresponding to position 136 is substituted with another amino acid.

The protein variant, in which the amino acid at position 136 from the N-terminus of the sequence of SEQ ID NO: 1 is substituted with another amino acid, may include an amino acid sequence of SEQ ID NO: 12, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, or SEQ ID NO: 63, specifically, may consist essentially of any one of amino acid sequences of SEQ ID NO: 12, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO: 63, and more specifically, may consist of any one of amino acid sequences of SEQ ID NO: 12, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO: 63, but is not limited thereto.

Further, the protein variant may include any one amino acid sequence of SEQ ID NO: 12, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO: 63, or may include an amino acid sequence having 80% or more homology or identity to the amino acid sequence of SEQ ID NO: 1, provided that the amino acid at position 136 from the N-terminus of the amino acid sequence of SEQ ID NO: 1 is not changed, but is not limited thereto. Specifically, the variant polypeptide of the present disclosure may include a polypeptide having at least 80%, 90%, 95%, 96%, 97%, 98%, or 99% homology or identity to any one amino acid sequence of SEQ ID NO: 12, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO: 63, and to any one amino acid sequence of SEQ ID NO: 12, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO: 63. Further, it is apparent that any protein having an amino acid sequence, part of which is deleted, modified, substituted, or added, in addition to the amino acid at position 136, may also be within the scope of the present disclosure, as long as the protein has such a homology or identity and exhibits efficacy corresponding to that of the above protein.

As used herein, the term "homology" or "identity" refers to a degree of matching between two given amino acid sequences or nucleotide sequences, and nay be expressed as a percentage. The terms "homology" and "identity" may often be used interchangeably with each other. The sequence homology or identity of the conserved polynucleotide or polypeptide may be determined by standard alignment algorithms, and may be used with default gap penalties established by the program used. Substantially, homologous or identical sequences may hybridize under moderately or highly stringent conditions such that the full length of the sequence or at least about 50%, 60%, 70%, 80%, or 90% or more of the full length may hybridize. In addition, contemplated are polynucleotides that contain degenerate codons in place of codons in the hybridization.

Whether or not any two polynucleotide or polypeptide sequences have homology, similarity, or identity may be determined using known computer algorithms such as the "FASTA" program, using, for example, the default parameters as in Pearson et al. (1988) [Proc. Natl. Acad. Sci. USA 85]: 2444, or determined using the Needleman-Wunsch algorithm (Needleman and Wunsch, 1970, J. Mol. Biol. 48: 443-453) as implemented in the Needleman program of the EMBOSS package (EMBOSS: The European Molecular Biology Open Software Suite, Rice et al., 2000, Trends Genet. 16: 276-277) (version 5.0.0 or later) (including GCG program package (Devereux, J. et al., Nucleic Acids Research 12: 387 (1984)), BLASTP, BLASTN, FASTA (Atschul, [S.][F.,][ET AL, J MOLEC BIOL 215]: 403 (1990); Guide to Huge Computers, Martin J. Bishop, [ED.,] Academic Press, San Diego,1994, and [CARILLO ETA/.] (1988) SIAM J Applied Math 48: 1073). For example, BLAST of the National Center for Biotechnology Information database, or ClustalW may be used to determine homology, similarity, or identity.

Homology, similarity, or identity of polynucleotides or polypeptides may be determined, for example, by comparing sequence information using a GAP computer program such as Needleman et al. (1970), J Mol Biol. 48: 443, as disclosed in Smith and Waterman, Adv. Appl. Math (1981) 2:482. Briefly, the GAP program defines similarity as the number of aligned symbols (i.e., nucleotides or amino acids), which are similar, divided by the total number of symbols in the shorter of the two sequences. Default parameters for the GAP program may include: (1) a unary comparison matrix (containing a value of 1 for identities and 0 for non-identities) and the weighted comparison matrix of Gribskov et al. (1986) Nucl. Acids Res. 14: 6745, as disclosed in Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or gap open penalty of 10, gap extension penalty of 0.5); and (3) no penalty for end gaps.

Further, whether or not any two polynucleotide or polypeptide sequences have homology, similarity, or identity may be determined by comparing sequences by Southern hybridization experiments under defined stringent conditions, and the defined appropriate hybridization conditions may be within the technical scope of the art and may be determined by a method well known to those skilled in the art (e.g., J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York)

Another aspect of the present disclosure provides a polynucleotide encoding the protein variant.

As used herein, the term "polynucleotide" refers to a DNA or RNA strand having a predetermined length or more, which is a long-chain polymer of nucleotides formed by linking nucleotide monomers via covalent bonds. More specifically, the polynucleotide refers to a polynucleotide fragment encoding the protein variant.

The polynucleotide encoding the protein variant of the present disclosure may include any polynucleotide sequence without limitation, as long as it is a polynucleotide sequence encoding the protein variant having acetohydroxy acid synthase activity.

In the present disclosure, the gene encoding the amino acid sequence of the protein having acetohydroxy acid synthase activity may be ilvB gene, and may be derived from *Corynebacterium glutamicum*. Specifically, the gene may be a nucleotide sequence encoding the amino acid sequence of SEQ ID NO: 1, but is not limited thereto.

Specifically, the polynucleotide encoding the protein variant of the present disclosure may include any polynucleotide sequence without limitation, as long as it encodes the protein variant in which the amino acid at position 136 in the amino acid sequence of SEQ ID NO: 1 is substituted with another amino acid. For example, the polynucleotide of the present disclosure may be a polynucleotide sequence encoding the protein variant of the present disclosure, specifically, a protein including any one amino acid sequence of SEQ ID NO: 12, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO: 63, or a polypeptide having homology or identity thereto, but is not limited thereto. The homology or identity is the same as described above.

Additionally, in the polynucleotide encoding the protein variant, various modifications may be made in the coding region provided that they do not change the amino acid sequence of the polypeptide, due to codon degeneracy or in consideration of the codons preferred by the organism in which the polypeptide is to be expressed.

Further, the polynucleotide encoding the protein variant may include a probe which may be produced from a known nucleotide sequence, for example, any probe without limitation as long as it includes a sequence which hybridizes with a sequence complementary to all or a part of the polynucleotide sequence under stringent conditions to encode the protein variant in which another amino acid is substituted for the amino acid at position 136 in the amino acid sequence of SEQ ID NO: 1.

The term "stringent conditions" means conditions under which specific hybridization between polynucleotides is allowed. Such conditions are described in detail in the literature (e.g., J. Sambrook et al., supra). For example, the stringent conditions may include conditions under which genes having high homology of 40% or higher, specifically 90% or higher, more specifically 95% or higher, much more specifically 97% or higher, particularly specifically 99% or higher homology are hybridized with each other, and genes having homology lower than the above homology are not hybridized with each other, or ordinary washing conditions of Southern hybridization, i.e., washing once, specifically, twice or three times at a salt concentration and a temperature corresponding to 60° C. 1×SSC, 0.1% SDS, specifically, 60° C. 0.1×SSC, 0.1% SDS, and more specifically 68° C. 0.1×SSC, 0.1% SDS. However, the stringent conditions are not limited thereto, and may be appropriately controlled by one of ordinary skill in the art according to the purposes.

Although mismatch between nucleotides may occur due to the stringency of hybridization, it is required that the two polynucleotides have a complementary sequence. The term "complementary" is used to describe the relationship between nucleotide bases which may hybridize with each other. For example, with respect to DNA, adenosine is complementary to thymine, and cytosine is complementary to guanine. Accordingly, the present disclosure may include not only the substantially similar polynucleotide sequences but also isolated polynucleotide fragments which are complementary to the entire sequence.

Specifically, the polynucleotide having homology may be detected using hybridization conditions including the hybridization at a $T_m$ value of 55° C. and the conditions described above. Additionally, the $T_m$ value may be 60° C., 63° C., or 65° C., but is not limited thereto, and may be appropriately controlled by one of ordinary skill in the art according to the purposes.

Appropriate stringency for the hybridization of polynucleotides depends on the length and degree of complementarity of the polynucleotides, and the variables are well known in the art (see Sambrook et al., supra, 9.50-9.51, 11.7-11.8).

Still another aspect of the present disclosure provides a vector including the polynucleotide encoding the protein variant.

As used herein, the term "vector" refers to a DNA construct that includes a nucleotide sequence of a polynucleotide encoding a target protein operably linked to an appropriate regulatory sequence to enable expression of the target protein in an appropriate host cell. The regulatory sequence may include a promoter capable of initiating transcription, any operator sequence for the regulation of such transcription, a sequence encoding an appropriate mRNA ribosome-binding domain, and a sequence regulating termination of transcription and translation. After the vector is transformed into the appropriate host cell, it may replicate or function independently of the host genome, and may be integrated into the genome itself.

As used herein, the term "operably linked" means a functional linkage between a promoter sequence which initiates and mediates transcription of the polynucleotide encoding the target protein of the present disclosure and the polynucleotide sequence. The operable linkage may be prepared using a gene recombinant technique known in the art, and site-specific DNA cleavage and linkage may be prepared using enzymes for cleavage and ligation known in the art, etc., but is not limited thereto.

The vector used in the present disclosure is not particularly limited, as long as it is able to replicate in the host cell, and any vector known in the art may be used. Examples of commonly used vectors may include a natural or recombinant plasmid, cosmid, virus, and bacteriophage. For instance, pWE15, M13, MBL3, MBL4, IXII, ASHII, APII, t10, t11, Charon4A, Charon21A, etc. may be used as a phage vector or cosmid vector. As a plasmid vector, pBR type, pUC type, pBluescriptII type, pGEM type, pTZ type, pCL type, pET type, etc. may be used. Specifically, pDZ, pACYC177, pACYC184, pCL, pECCG117, pUC19, pBR322, pMW118, pCC1BAC vector, etc. may be used.

For example, a polynucleotide encoding a target protein in the chromosome may be replaced by a mutated polynucleotide using a vector for intracellular chromosomal insertion. The chromosomal insertion of the polynucleotide may be performed by any method known in the art, for example, homologous recombination, but is not limited thereto. A selection marker to confirm the chromosomal insertion may be further included. The selection marker is to select cells transformed with the vector, that is, to confirm insertion of the target nucleic acid molecule, and the selection marker may include markers providing selectable phenotypes, such as drug resistance, auxotrophy, resistance to cytotoxic agents, or expression of surface proteins. Since only cells expressing the selection marker are able to survive or to show different phenotypes under the environment treated with a selective agent, the transformed cells may be selected.

As used herein, the term "transformation" means the introduction of a vector including a polynucleotide encoding a target protein into a host cell in such a way that the protein encoded by the polynucleotide is expressed in the host cell. As long as the transformed polynucleotide may be expressed in the host cell, it does not matter whether the transformed polynucleotide may be integrated into and placed in the chromosome of the host cell, or it may exist extrachromosomally. Further, the polynucleotide includes DNA and RNA encoding the target protein. The polynucleotide may be introduced in any form, as long as it may be introduced into the host cell and expressed therein. For example, the polynucleotide may be introduced into the host cell in the form of an expression cassette, which is a gene construct including all elements required for its autonomous expression. Commonly, the expression cassette may include a promoter operably linked to the polynucleotide, transcriptional termination signals, ribosome binding sites, and translation termination signals. The expression cassette may be in the form of a self-replicable expression vector. Additionally, the polynucleotide as it is may be introduced into the host cell and operably linked to sequences required for expression in the host cell, but is not limited thereto. The transformation method includes any method of introducing a polynucleotide into a cell, and may be performed by selecting a suitable standard technique known in the art, depending on the host cell. For example, the method may include electroporation, calcium phosphate ($Ca(H_2PO_4)_2$, $CaHPO_4$, or $Ca_3(PO_4)_2$) precipitation, calcium chloride ($CaCl_2$)) precipitation, microinjection, a polyethylenegly col (PEG) method, a DEAE-dextran method, a cationic liposome method, a lithium acetate-DMSO method, etc., but the method is not limited thereto.

Still another aspect of the present disclosure provides a microorganism including the protein variant having acetohydroxy acid synthase activity. Specifically, the microorganism may be a microorganism producing L-isoleucine, which expresses the protein variant having acetohydroxy acid synthase activity of the present disclosure.

As used herein, the term "protein allowed to be expressed/ to be expressed/expressed" refers to a state in which the target protein is introduced into the microorganism or is modified to be expressed in the microorganism. When the target protein is a protein present in the microorganism, it means a state in which its activity is enhanced, as compared with the endogenous activity or activity before modification. With respect to the objects of the present disclosure, the "target protein" may be a variant of the protein having acetohydroxy acid synthase activity described above.

Specifically, "introduction of the protein" means that a microorganism exhibits activity of a particular protein that was not originally possessed, or exhibits enhanced activity, as compared with the endogenous activity of the corresponding protein or the activity before modification. For example, a polynucleotide encoding a particular protein may be introduced into a chromosome in a microorganism, or a vector containing a polynucleotide encoding a particular protein may be introduced into a microorganism to exhibit its activity. Further, the "enhancement of activity" means that particular protein activity of a microorganism is enhanced, as compared with its endogenous activity or activity before modification, or a feedback inhibition effect on a particular protein is released, and thus activity is not inhibited, as compared with its endogenous activity or activity before modification. The "endogenous activity" refers to activity of a particular protein originally possessed by a parent strain before transformation, when the microorganism's trait is changed due to genetic variation caused by natural or artificial factors.

Specifically, the enhancement of activity in the present disclosure may be achieved by any one method selected from the group consisting of methods of modifying a polynucleotide sequence, such as a method of increasing the copy number of a polynucleotide encoding the target protein in a cell, a method of introducing a modification in the expression regulatory sequence of the polynucleotide encoding the target protein, a method of substituting the expression regulatory sequence of the polynucleotide encoding the target protein with a sequence having strong activity, a method of substituting the polynucleotide encoding the target protein on the chromosome with a polynucleotide encoding a protein variant having enhanced activity, or a method of additionally introducing a mutation; and a method of introducing a protein variant into a microorganism, but is not limited thereto. The polynucleotide encoding the target protein may refer to a target gene.

In the above, the increase in the copy number of the polynucleotide, while not particularly limited thereto, may be performed in a state operably linked to a vector, or by being inserted into the chromosome within a host cell. Specifically, the method may be executed by introducing a vector into a host cell, the vector to which the polynucleotide encoding the protein of the present disclosure is operably linked, and which may replicate and function irrespective of a host; or introducing a vector into the chromosome of the host cell, the vector to which the polynucleotide is operably linked and capable of inserting the polynucleotide into the chromosome of the host cell. The insertion of the polynucleotide into the chromosome may be performed using a known method in the art, for example, by homologous recombination.

Next, the modification of the expression regulatory sequence for increasing expression of a polynucleotide, while not particularly limited thereto, may be performed by inducing a modification in the polynucleotide sequence via deletion, insertion, non-conservative or conservative substitution, or a combination thereof so as to further enhance the activity of the expression regulatory sequence, or by replacing the polynucleotide sequence with a nucleotide sequence with a stronger activity. The expression regulatory sequence may include, but is not particularly limited to, a promoter, an operator sequence, a sequence encoding a ribosome-binding domain, a sequence regulating termination of transcription and translation, etc.

The replacement with a nucleotide sequence with a stronger activity to further enhance the activity of the expression regulatory sequence is to connect a stronger promoter, instead of the original promoter, but is not limited thereto. Examples of the known strong promoters may include cj1 to cj7 promoters (Korean Patent No. 10-0620092), lac promoter, trp promoter, trc promoter, tac promoter, lambda phage PR promoter, PL promoter, tet promoter, gapA promoter, SPL7 promoter, SPL13(sm3) promoter (Korean Patent No. 10-1783170), 02 promoter (Korean Patent No. 10-1632642), tkt promoter, yccA promoter, etc., but the promoter is not limited thereto.

Additionally, the modification of the polynucleotide sequence on the chromosome, while not particularly limited thereto, may be performed by inducing a modification in the expression regulatory sequence via deletion, insertion, non-conservative or conservative substitution, or a combination thereof so as to further enhance the activity of the polynucleotide sequence, or by replacing the polynucleotide sequence with a polynucleotide sequence which is improved to have stronger activity.

Such introduction and enhancement of the protein activity may increase the activity or concentration of the corresponding protein relative to the activity or concentration of a protein of a wild-type or non-modified microorganism strain from at least 1%, 10%, 25%, 50%, 75%, 100%, 150%, 200%, 300%, 400%, or 500%, to a maximum of 1,000% or 2,000%, but is not limited thereto.

As used herein, the term "microorganism producing L-isoleucine" refers to a microorganism capable of producing a large amount of L-isoleucine from a carbon source in a medium, as compared with a wild-type or non-modified microorganism. Further, the microorganism producing L-isoleucine may be a recombinant microorganism. Specifically, the kind of the microorganism is not particularly limited, as long as it is able to produce L-isoleucine, and the microorganism may be a microorganism belonging to the genus *Enterobacter*, the genus *Escherichia*, the genus *Erwinia*, the genus *Serratia*, the genus *Providencia*, the genus *Corynebacterium*, or the genus *Brevibacterium*. More specifically, the microorganism may be a microorganism belonging to the genus *Corynebacterium* or the genus *Escherichia*.

Much more specifically, the microorganism belonging to the genus *Escherichia* may be *Escherichia coli*, and the microorganism belonging to the genus *Corynebacterium* may be *Corynebacterium glutamicum*. However, any microorganism belonging to the genus *Corynebacterium* or the genus *Escherichia* may be used without limitation, as long as its L-isoleucine productivity may be increased by introducing or enhancing the protein having acetohydroxy acid synthase activity.

In the present disclosure, a parent strain of the microorganism producing L-isoleucine which is modified to express the protein variant having acetohydroxy acid synthase activity is not particularly limited, as long as it is a microorganism producing L-isoleucine. The microorganism producing L-isoleucine may be a natural microorganism itself or a microorganism having improved L-isoleucine productivity by inserting an exogenous gene related to the L-isoleucine production mechanism or by enhancing or inactivating the activity of the endogenous gene.

Still another aspect of the present disclosure provides a method of producing L-isoleucine, the method including culturing, in a medium, a microorganism producing L-isoleucine, the microorganism expressing the protein variant having acetohydroxy acid synthase activity.

The L-isoleucine, the protein having acetohydroxy acid synthase activity including the amino acid sequence of SEQ ID NO: 1, the expression of the protein, and the microorganism are the same as described above.

As used herein, the "L-isoleucine" may include L-isoleucine itself as well as salts thereof.

As used herein, the term "culturing" refers to growing the microorganism in appropriately controlled environmental conditions. The culturing process of the present disclosure may be performed according to appropriate medium and culture conditions known in the art. The culturing process may be easily adjusted for use by a skilled person in the art according to the strain to be selected. Specifically, the culturing may be performed in a batch, continuous, or fed batch mode, but is not limited thereto.

As used herein, the term "medium" refers to a substance in which nutrients required for culturing the microorganism are mixed as main components, and supplies nutrients and growth factors, including water essential to survival and development. Specifically, the medium and other culture conditions used for culturing the microorganism of the present disclosure may be used without particular limitation as long as they are commonly used for culturing microorganisms. The microorganism of the present disclosure may be cultured in a common medium containing appropriate carbon sources, nitrogen sources, phosphorus sources, inorganic compounds, amino acids, and/or vitamins while controlling temperature, pH, etc. under aerobic conditions.

In the present disclosure, the carbon sources may include carbohydrates such as glucose, fructose, sucrose, maltose, etc.; sugar alcohols such as mannitol, sorbitol, etc.; organic acids such as pyruvate, lactate, citrate, etc.; and amino acids such as glutamic acid, methionine, lysine, etc. Additionally, natural organic nutrients such as starch hydrolysate, molasses, blackstrap molasses, rice bran, cassava, sugar cane molasses, corn steep liquor, etc., and specifically, carbohydrates such as glucose and sterile pretreated molasses (i.e., molasses converted to a reducing sugar), etc. may be used. Furthermore, various other carbon sources may be used in a suitable amount without limitation. These carbon sources may be used alone or in a combination of two or more thereof, but are not limited thereto.

The nitrogen sources may include inorganic nitrogen sources such as ammonia, ammonium sulfate, ammonium chloride, ammonium acetate, ammonium phosphate, ammonium carbonate, ammonium nitrate, etc.; amino acids such as glutamic acid, methionine, glutamine, etc.; and organic nitrogen sources such as peptone, NZ-amine, meat extract, yeast extract, malt extract, corn steep liquor, casein hydrolysate, fish or decomposition products thereof, defatted soybean cake or decomposition products thereof, etc. These nitrogen sources may be used alone or in a combination of two or more thereof, but are not limited thereto.

The phosphorus sources may include potassium phosphate monobasic, dipotassium phosphate dibasic, corresponding sodium-containing salts, etc. The inorganic compounds may include sodium chloride, calcium chloride, iron chloride, magnesium sulfate, manganese sulfate, calcium carbonate, etc., and additionally, amino acids, vitamins, and/or suitable precursors may be included. These components or precursors may be added to a medium in a batch or continuous mode, but are not limited thereto.

In the present disclosure, pH of the medium may be adjusted during the culture of the microorganism by adding a compound such as ammonium hydroxide, potassium hydroxide, ammonia, phosphoric acid, sulfuric acid, etc. to the medium in an appropriate manner. Additionally, during the culture, an anti-foaming agent such as a fatty acid polyglycol ester may be used to inhibit the formation of foam. Additionally, oxygen or oxygen-containing gas may be injected into the medium in order to maintain an aerobic state of the medium; or nitrogen, hydrogen, or carbon dioxide gas may be injected, or no gas may be injected, in order to maintain an anaerobic or microaerobic state, but the culturing is not limited thereto.

A temperature of the medium may be 20° C. to 50° C., and specifically, 30° C. to 37° C., but is not limited thereto. The culturing may be continued until the desired amount of useful materials produced is obtained, specifically, for 10 hours to 100 hours, but is not limited thereto.

The production method may further include recovering L-isoleucine from the medium or the microorganism according to the culturing.

The recovery of L-isoleucine may be performed by recovering the desired L-isoleucine from the medium using an appropriate method known in the art according to the method of culturing the microorganism of the present disclosure, for example, a batch, continuous, fed batch method, etc. For example, centrifugation, filtration, treatment with a protein crystallizing precipitant (salting-out method), extraction, sonication, ultrafiltration, dialysis, various kinds of chromatography, e.g., molecular sieve chromatography (gel filtration), adsorption chromatography, ion-exchange chromatography, affinity chromatography, etc., HPLC, and a combination thereof may be used, but the recovery is not limited thereto.

The production method may include a purification process. The purification process may be performed to purify the recovered L-isoleucine by using an appropriate method known in the art.

Still another aspect of the present disclosure provides a method of increasing L-isoleucine productivity, the method including modifying a microorganism to express the protein variant having acetohydroxy acid synthase activity, wherein the amino acid at position 136 in the amino acid sequence of SEQ ID NO: 1 is substituted with another amino acid.

Still another aspect of the present disclosure provides use of the protein variant for increasing L-isoleucine productivity.

The protein variant and another amino acid are the same as described above.

Advantageous Effects

When a microorganism including the acetohydroxy acid synthase variant of the present disclosure is cultured, it is possible to produce L-isoleucine in a high yield. Accordingly, from an industrial point of view, it is possible to expect the effects of production convenience and reduction of production costs.

DETAILED DESCRIPTION OF THE INVENTION

Hereinafter, the present disclosure will be described in more detail with reference to the following Examples. However these Examples are for illustrative purposes only, and the scope of the present disclosure is not intended to be limited by these Examples.

Example 1. Selection of Random Mutant Strains by Artificial Mutagenesis

In this Example, in order to obtain a microorganism mutant strain having an enhanced ability to produce L-isoleucine, a mutation in a microorganism was induced in the following manner.

First, in order to introduce, into a wild-type *Corynebacterium glutamicum* ATCC 13032 strain, ilvA(F383A) mutation for releasing feedback inhibition of L-threonine dehydratase (ilvA), which functions as an important enzyme in the biosynthesis of isoleucine, primers of SEQ ID NO: 72, SEQ ID NO: 73, SEQ ID NO: 74, and SEQ ID NO: 75 were prepared.

PCR was carried out using a genomic DNA of *Corynebacterium glutamicum* ATCC 13032 as a template and primers of SEQ ID NOS: 72 and 73 and SEQ ID NO: 74, and SEQ ID NO: 75. PCR was carried out using PfuUltra™ high-fidelity DNA polymerase (Stratagene), and PCR conditions were as follows: 25 cycles of denaturation at 95° C. for 30 seconds, annealing at 55° C. for 30 seconds, and polymerization at 72° C. for 1 minute. As a result, a 1,000 bp DNA fragment of the upstream region of ilvA gene, and a 1,000 bp DNA fragment of the downstream region of ilvA gene were obtained, and each amplification product was purified using a PCR purification kit of QIAGEN, and used as an insert DNA fragment for vector construction. After treatment with a restriction enzyme smaI, a pDZ vector (Korean Patent No. 0924065) which was heat-treated at 65° C. for 20 minutes and the DNA fragments were cloned at a molar concentration (M) of 1:2 using an Infusion Cloning Kit (TaKaRa) according to the manual provided, thereby constructing a pDZ-F383A vector for introducing an F383A mutation on the chromosome.

The constructed vector was transformed into *Corynebacterium glutamicum* ATCC 13032 by electroporation. Through a secondary crossover process, a strain in which each mutant base was substituted on the chromosome was obtained. Whether or not the substitution properly occurred was primarily determined using the following primer combinations and Mutant Allele Specific Amplification (MASA) PCR technique (Takeda et al., Hum. Mutation, 2, 112-117 (1993)) by selecting a strain which was amplified by a primer combination (SEQ ID NO: 68 and SEQ ID NO: 76) corresponding to the mutated sequence, and the ilvA sequence of the selected strain was analyzed using a primer combination of SEQ ID NO: 77 and SEQ ID NO: 78 to secondarily confirm the mutated sequence.

Next, in order to prepare a strain in which hom(R407H) (Korean Patent No. 10-1996769) mutation was additionally introduced into the ilvA(F383A) mutant-introduced strain, primers of SEQ ID NO: 64, SEQ ID NO: 65, SEQ ID NO: 66, and SEQ ID NO: 67 were prepared.

PCR was carried out using genomic DNA extracted from *Corynebacterium glutamicum* ATCC 13032 as a template and primers of SEQ ID NO: 64, SEQ ID NO: 65, SEQ ID NO: 66, and SEQ ID NO: 67. PCR was carried out using PfuUltra™ high-fidelity DNA polymerase (Stratagene), and PCR conditions were as follows: 25 cycles of denaturation at 95° C. for 30 seconds, annealing at 55° C. for 30 seconds, and polymerization at 72° C. for 1 minute. As a result, a 1,000 bp DNA fragment of the upstream region of hom gene, and a 1,000 bp DNA fragment of the downstream region of hom gene were obtained, and each amplification product was purified using a PCR purification kit of QIAGEN, and used as an insert DNA fragment for vector construction. Meanwhile, after treatment with a restriction enzyme smaI, a pDZ vector (Korean Patent No. 0924065) which was heat-treated at 65° C. for 20 minutes and the insert DNA fragment amplified by PCR were cloned at a molar concentration (M) of 1:2 using an Infusion Cloning Kit (TaKaRa) according to the manual provided, thereby constructing a pDZ-R407H vector for introducing an R407H mutation on the chromosome.

The constructed vector was transformed into *Corynebacterium glutamicum* ATCC 13032 ilvA(F383A) by electroporation. Through a secondary crossover process, a strain in which each mutant base was substituted on the chromosome was obtained. Whether or not the substitution properly occurred was primarily determined using the following primer combinations and Mutant Allele Specific Amplification (MASA) PCR technique (Takeda et al., Hum. Mutation, 2, 112-117 (1993)) by selecting a strain which was amplified by a primer combination (SEQ ID NO: 68 and SEQ ID NO: 69) corresponding to the mutated sequence, and the hom sequence of the selected strain was analyzed using a primer combination of SEQ ID NO: 70 and SEQ ID NO: 71 to secondarily confirm the mutated sequence.

Specifically, *Corynebacterium glutamicum* ATCC 13032 hom(R407H) ilvA(F383A), which is a parent strain, was cultured in an activation medium for 16 hours, and the activated strain was inoculated into a seed medium, which was sterilized at 121° C. for 15 minutes, and cultured for 14 hours, and 5 mL of the culture was recovered. The recovered culture was washed with 100 mM citric acid buffer, and N-methyl-N-nitro-N-nitrosoguanidine (NTG) was added thereto to a final concentration of 200 mg/L and treated for 20 minutes, and washed with 100 mM phosphate buffer. The strain treated with NTG was plated on a minimal medium and the death rate was calculated, and as a result, the death rate was 85%. The surviving cells were inoculated and cultured in the seed medium, and finally, a mutant strain showing an excellent ability to produce isoleucine was selected and designated as *Corynebacterium glutamicum* CJILE-42 (CJILE-42).

Compositions of the media used in Example 1 are as follows:

<Activation Medium>

Beef Extract 1%, Polypeptone 1%, Sodium Chloride 0.5%, Yeast Extract 1%, Agar 2%, pH 7.2

<Seed Medium>

Glucose 5%, Bactopeptone 1%, Sodium Chloride 0.25%, Yeast Extract 1%, Urea 0.4%, pH 7.2

<Minimal Medium>

Glucose 1.0%, Ammonium Sulfate 0.4%, Magnesium Sulfate 0.04%, Monopotassium Phosphate 0.1%, Urea 0.1%, Thiamine 0.001%, Biotin 200 μg/L, Agar 2%, pH 7.2

Example 2: Examination of L-Isoleucine Productivity of Random Mutant Strain Producing L-Isoleucine To examine L-isoleucine productivity of *Corynebacterium glutamicum* CJILE-42, which is the mutant strain obtained in Example 1, the strain was cultured by the following method. The parent strain and the mutant strain were each inoculated into 250 mL corner-baffle flasks containing 25 mL of a production medium and cultured in a shaking incubator at 200 rpm at 32° C. for 60 hours to produce L-isoleucine.

A composition of the production medium used in Example 2 is as follows:

<Production Medium>

Glucose 10%, Yeast Extract 0.2%, Ammonium Sulfate 1.6%, Monopotassium Phosphate 0.1%, Magnesium Sulfate Heptahydrate 0.1%, Ferrous Sulfate Heptahydrate 10 mg/L, Manganese Sulfate Monohydrate 10 mg/L, Biotin 200 μg/L, pH 7.2

After completing the culture, the amount of L-isoleucine produced was measured using high-performance liquid chromatography(HPLC), and the L-isoleucine concentration in the culture medium for each strain was shown in Table 1 below.

TABLE 1

| Comparison of L-isoleucine productivity between parent strain and CJILE-42 | | |
|---|---|---|
| | *Corynebacterium glutamicum* ATCC 13032 hom(R407H) ilvA(F383A) (parent strain) | *Corynebacterium glutamicum* CJILE-42 (mutant strain) |
| L-Isoleucine concentration (g/L) | 0.2 | 1.8 |

As a result, as shown in Table 1, the parent strain *Corynebacterium glutamicum* ATCC 13032 hom(R407H) ilvA(F383A) produced L-isoleucine at a concentration of 0.2 g/L, whereas *Corynebacterium glutamicum* CJILE-42, which is the mutant strain according to the present disclosure, produced L-isoleucine at a concentration of 1.8 g/L, indicating an about 9-fold or more increase in the L-isoleucine productivity as compared with the parent strain.

Based on the result above, genomic sequencing of the genes in the synthesis pathway of L-isoleucine from L-threonine was performed. As a result, random mutation was observed in ilvB gene of ilvBN exhibiting acetohydroxy acid synthase (AHAS) activity, and this mutant ilvB gene was represented by SEQ ID NO: 2.

From the result above, it was confirmed that the mutant strain obtained by random mutagenesis is able to produce L-isoleucine with high efficiency and high yield without feedback inhibition.

Example 3: Preparation of ilvBNC-Deleted Strain for Comparison of Acetohydroxy Acid Synthase (AHAS) Activity In order to evaluate activity of the mutant ilvB having acetohydroxy acid synthase (AHAS) activity, an ilvBNC-deleted strain was prepared, in which the strain is not able to convert pyruvate and 2-ketobutyrate as substrates into 2-aceto-2-hydroxyacetate due to lack of acetohydroxy acid synthase (AHAS) activity. Although it was intended to measure the activity of ilvB, expression of ilvB, ilvC, and ilvN genes are uniformly regulated because these three genes are adjacent to each other as an operon in *Corynebacterium glutamicum*. Therefore, in order to delete the ilvBNC gene, a pair of primers (SEQ ID NOS: 3 and 4) for amplifying the 5'-upstream region of the ilvBNC gene, and a pair of primers (SEQ ID NOS: 5 and 6) for amplifying the 3'-downstream region of the ilvBNC gene were designed, based on the nucleotide sequence information of WT-derived ilvBNC gene. At each end of the primers of SEQ ID NOS: 3 and 6, the XbaI restriction site (underlined) was inserted. Each sequence is shown in Table 2 below.

TABLE 2

| SEQ ID NO: | Sequence (5'-3') |
|---|---|
| 3 | ATTCTAGAGGCCAAGAAGTCCGC |
| 4 | CTTGTTGCTGCTACACACATCGAGTTTCC |
| 5 | TGTAGCAGCAACAAGATTTTGGCAAAATG |
| 6 | ATTCTAGAGCCGAACGGCGCCCC |

17

PCR was carried out using the chromosome of *Coryne-bacterium glutamicum* ATCC 13032 hom(R407H) ilvA (F383A) as a template and primers of SEQ ID NO: 3, SEQ ID NO: 4, SEQ ID NO: 5, and SEQ ID NO: 6. As a polymerase, Solg™ Pfu-X DNA polymerase (SolGent co., Ltd.) was used, and PCR conditions were as follows: denaturation at 95° C. for 10 minutes; 30 cycles of denaturation at 95° C., annealing at 56° C., and polymerization at 72° C. for 45 seconds; and polymerization at 72° C. for 5 minutes. As a result, a 500 bp DNA fragment of the 5'-upstream region of ilvBNC gene and a 500 bp DNA fragment of the 3'-downstream region of ilvBNC gene were obtained.

PCR was carried out using the amplified two DNA fragments as a template and primers of SEQ ID NO: 3 and SEQ ID NO: 6. As a polymerase, Solg™ Pfu-X DNA polymerase (SolGent co., Ltd.) was used, and PCR conditions were as follows: denaturation at 95° C. for 10 minutes; 30 cycles of denaturation at 95° C., annealing at 56° C., and polymerization at 72° C. for 1 minute; and polymerization at 72° C. for 5 minutes. As a result, a 1,006 bp DNA fragment including only the upstream and downstream regions due to the deletion of ilvBNC gene was amplified.

The pDZ vector and the 1,006 bp DNA fragment were treated with restriction enzyme XbaI, and ligated using a DNA ligase, and then cloned to obtain a plasmid, which was designated as pDZ-ΔilvBNC.

The pDZ-ΔilvBNC vector was introduced into the *Corynebacterium glutamicum* ATCC 13032 hom(R407H) ilvA(F383A) strain by an electric pulse method, and then a transformed strain was obtained in a selection medium containing 25 mg/L of kanamycin. WTΔilvBNC, which is the ilvBNC gene-deleted strain resulting from insertion of the DNA fragment onto the chromosome by the secondary crossover process, was obtained.

Example 4: Construction of Wild-Type ilvBNC
Plasmid Having Acetohydroxy Acid Synthase
(AHAS) Activity In order to amplify a gene encoding acetohydroxy acid synthase (AHAS) (ilvBNC), the BamHI restriction site (underlined) was inserted at both ends of primers (SEQ ID NOS: 8 and 9) for amplifying from the promoter region (about 300 bp upstream from the initiation codon) to the terminator region (about 100 bp downstream from the termination codon), based on the sequence (SEQ ID NO: 7) derived from *Corynebacterium glutamicum* ATCC 13032 hom(R407H) ilvA(F383A). The corresponding sequences are shown in Table 3 below.

TABLE 3

| SEQ ID NO: | Sequence (5'-3') |
|---|---|
| 8 | TCCGGATCCTGACACACCATGACCATTATTC |
| 9 | TCCGGATCCCTTATGTACAAAGTGCACAGC |

As a polymerase, Solg™ Pfu-X DNA polymerase (SolGent co., Ltd.) was used, and PCR conditions were as follows: denaturation at 95° C. for 10 minutes; 30 cycles of denaturation at 95° C. for 30 seconds, annealing at 56° C. for 30 seconds, and polymerization at 72° C. for 4 minutes; and polymerization at 72° C. for 7 minutes. As a result, a 4,010 bp DNA fragment of the coding region of ilvBNC gene was obtained. The pECCG117 vector (Korean Patent No. 10-0057684) and the ilvBN DNA fragment were treated with restriction enzyme BamHI, and ligated using a DNA ligase, and then cloned to obtain a plasmid, which was designated as pECCG117-ilvBNC WT.

Example 5: Construction of Mutant ilvBNC
Plasmid Having Acetohydroxy Acid Synthase
(AHAS) Activity In order to compare activity of the mutant ilvB producing a large amount of L-isoleucine, a pair of primers (SEQ ID NOS: 8 and 10) for amplifying the 5'-upstream region of the mutation site, and a pair of primers (SEQ ID NOS: 11 and 9) for amplifying the 3'-downstream region of the mutation site were designed to construct a mutant-introduced vector with respect to *Corynebacterium glutamicum* ATCC 13032 hom(R407H) ilvA(F383A)-derived acetohydroxy acid synthase (HAS) (SEQ ID NO: 7)-encoding ilvB gene. BamHI restriction sites (underlined) were inserted at each end of primers of SEQ ID NOS: 8 and 9. Primers of SEQ ID NOS: 10 and 11 were prepared such that the nucleotide substitution mutation (underlined) was located at a site designed to cross each other.

TABLE 4

| SEQ ID NO: | Sequence (5'-3') |
|---|---|
| 8 | TCCGGATCCTGACACACCATGACCATTATTC |
| 10 | CTTCgttGAAAGCGTCGGTACCCAG |
| 11 | CTTTCaacGAAGCCGATATCCGCGG |
| 9 | TCCGGATCCCTTATGTACAAAGTGCACAGC |

PCR was carried out using the chromosome of *Coryne-bacterium glutamicum* ATCC 13032 hom(R407H) ilvA (F383A) as a template and primers of SEQ ID NO: 8, SEQ ID NO: 10, SEQ ID NO: 11, and SEQ ID NO: 9. As a polymerase, Solg™ Pfu-X DNA polymerase (SolGent co., Ltd.) was used, and PCR conditions were as follows: denaturation at 95° C. for 10 minutes; 30 cycles of denaturation at 95° C. for 30 seconds, annealing at 56° C. for 30 seconds, and polymerization at 72° C. for 3 minutes; and polymerization at 72° C. for 5 minutes. As a result, a 712 bp DNA fragment of the 5'-upstream region of the mutation of ilvBNC gene and a 3,310 bp DNA fragment of the 3'-downstream region of the mutation of the ilvBNC gene were obtained.

PCR was carried out using the amplified two DNA fragments as templates and primers of SEQ ID NO: 8 and SEQ ID NO: 9. PCR conditions were as follows: denaturation at 95° C. for 10 minutes; 30 cycles of denaturation at 95° C. for 30 seconds, annealing at 56° C. for 30 seconds, and polymerization at 72° C. for 4 minutes; and polymerization at 72° C. for 7 minutes.

As a result, a 4,010 bp DNA fragment was amplified, which includes the mutant ilvB gene (SEQ ID NO: 2) encoding the acetohydroxy acid synthase (AHAS) variant (SEQ ID NO: 12), in which glutamine at position 136 was substituted with asparagine.

The pECCG117 vector (Korean Patent No. 10-0057684) and the ilvBN DNA fragment were treated with restriction enzyme BamHI and ligated using a DNA ligase, and then cloned to obtain a plasmid, which was designated as pECCG117-ilvB(Q136N)NC.

Example 6: Comparative Experiment of Activities of Wild-Type and Mutant ilvB Having Acetohydroxy Acid Synthase (AHAS) Activity The pECCG117-ilvBNC WT and pECCG117-ilvB (Q136N)NC vectors, each prepared in Examples 4 and 5, were introduced into the WTΔilvBNC strain prepared in Example 3 by an electric pulse method, and then each was plated on a selection medium containing 25 mg/L of kanamycin to obtain a transformant.

In order to compare L-isoleucine productivities of the prepared strains as above, the strains were cultured by the following method, and the concentration of L-isoleucine in the culture medium was analyzed.

One platinum loop of each strain was inoculated into a 250 mL corner-baffle flask containing 25 mL of the following medium and cultured in a shaking incubator at 200 rpm at 32° C. for 50 hours. The concentrations of L-isoleucine were analyzed by HPLC, and the analyzed concentrations are as shown in Table 5.

<Medium Composition (pH 7.0)>

Glucose 100 g, $(NH_4)_2SO_4$ 40 g, Soybean Protein 2.5 g, Corn Steep Solids 5 g, Urea 3 g, $KH_2PO_4$ 1 g, $MgSO_4·7H_2O$ 0.5 g, Biotin 100 μg, Thiamine HCl 1,000 μg, Calcium-Pantothenic Acid 2,000 μg, Nicotinamide 3,000 μg, $CaCO_3$ 30 g (based on 1 L of distilled water).

TABLE 5

| Strain | L-Isoleucine (g/L) | | |
| --- | --- | --- | --- |
| | Batch 1 | Batch 2 | Batch 3 |
| ATCC 13032 hom(R407H) ilvA(F383A) | 0.21 | 0.19 | 0.22 |
| ATCC 13032 hom(R407H) ilvA(F383A) ΔilvBNC | 0 | 0 | 0 |
| ATCC 13032 hom(R407H) ilvA(F383A) ΔilvBNC/ pECCG117-ilvBNC WT | 0.23 | 0.22 | 0.24 |
| ATCC 13032 hom(R407H) ilvA(F383A) ΔilvBNC/ pECCG117-ilvB(Q136N)NC | 3.12 | 3.24 | 3.21 |

Referring to Table 5 above, the strain introduced with the ilvB(Q136N) mutant plasmid showed an at least 13-fold increase in the L-isoleucine production, as compared with the strain introduced with the control ilvBNC WT plasmid. That is, the mutant-introduced strain had enhanced aceto-hydroxy acid synthase (AHAS) activity, thereby producing L-isoleucine with high efficiency and in high yield. The mutant Q136N-introduced strain was designated as CA10-3106. The CA10-3106 was deposited to the Korean Culture Center of Microorganisms, which is an international deposi-tory authority under the Budapest Treaty, on Dec. 3, 2018, with Accession No. KCCM12415P.

The KCCM11248P strain is a mutant strain (*Corynebac-terium glutamicum* KCJI-38, KCCM11248P; Korean Patent No. 10-1335789) showing common resistance to α-amino-β-hydroxynorvaline, which is an L-threonine derivative, and 4-thiaisoleucine and isoleucine-hydroxamate, which are L-isoleucine derivatives, in *Corynebacterium glutamicum* KFCC 11040 (Korean Patent Publication No. 2000-0002407), and the strain was confirmed to produce L-iso-leucine in high yield, as compared with *Corynebacterium glutamicum* ATCC 13032 hom(R407H) ilvA(F383A).

To examine the effect of the ilvB variant in the strain producing a larger amount of L-isoleucine, the KCCM11248P ΔilvBNC strain was prepared in the same manner as in Example 3. Further, the pECCG117-ilvBNC WT and pECCG117-ilvB(Q136N)NC vectors, prepared in Examples 4 and 5, respectively, were introduced into *Corynebacterium glutamicum* KCJI-38 (KCCM11248P), which is a strain having an enhanced ability to produce isoleucine, by an electric pulse method, and then each was plated on a selection medium containing 25 mg/L of kanamycin to obtain a transformant.

To compare L-isoleucine productivities of the prepared strains as above, the strains were cultured in the same manner as in Example 6. The concentrations of L-isoleucine in the culture medium were analyzed, and the analyzed concentrations are as shown in Table 6.

TABLE 6

| Strain | L-Isoleucine (g/L) | | |
| --- | --- | --- | --- |
| | Batch 1 | Batch 2 | Batch 3 |
| *Corynebacterium glutamicum* KCJI-38 (KCCM11248P) | 0.92 | 0.87 | 0.84 |
| KCCM11248PΔilvBNC | 0 | 0 | 0 |
| KCCM11248PΔilvBNC/ pECCG117-ilvBNC WT | 1.21 | 1.4 | 1.28 |
| KCCM11248PΔilvBNC/ pECCG117-ilvB(Q136N)NC | 7.48 | 7.16 | 7.79 |

Referring to Table 6 above, the strain introduced with the ilvB(Q136N) mutant plasmid showed an about 6-fold increase in the L-isoleucine production as compared with the strain introduced with the control ilvBNC WT plasmid. That is, the mutant-introduced strain had enhanced acetohydroxy acid synthase (AHAS) activity, thereby producing L-isoleu-cine with high efficiency and in high yield.

Example 7: Construction of Mutant ilvBNC Plasmid Having Acetohydroxy Acid Synthase (AHAS) Activity In order to examine that position 136, which was con-firmed in Example 6 as the ilvB mutation site with high L-isoleucine productivity, is an important position for increasing productivity, mutant types having different amino acid substitutions were prepared, and the effects thereof were confirmed. 17 mutants, each in which the amino acid at position 136 of ilvB was substituted with another amino acid, were additionally prepared, and the plasmid prepared in Example 4 was used as a template. Respective mutants, substituted amino acids, and primers used in each mutant are shown in Table 7 below.

TABLE 7

| Mutant plasmid | Substituted amino acid | SEQ ID NO of primer |
| --- | --- | --- |
| 136 mutation | Q136R | SEQ ID NO: 8, 13/SEQ ID NO: 14, 9 |
| | Q136F | SEQ ID NO: 8, 15/SEQ ID NO: 16, 9 |
| | Q136S | SEQ ID NO: 8, 17/SEQ ID NO: 18, 9 |
| | Q136Y | SEQ ID NO: 8, 19/SEQ ID NO: 20, 9 |
| | Q136C | SEQ ID NO: 8, 21/SEQ ID NO: 22, 9 |
| | Q136P | SEQ ID NO: 8, 23/SEQ ID NO: 24, 9 |
| | Q136H | SEQ ID NO: 8, 25/SEQ ID NO: 26, 9 |
| | Q136L | SEQ ID NO: 8, 27/SEQ ID NO: 28, 9 |
| | Q136I | SEQ ID NO: 8, 29/SEQ ID NO: 30, 9 |
| | Q136T | SEQ ID NO: 8, 31/SEQ ID NO: 32, 9 |
| | Q136K | SEQ ID NO: 8, 33/SEQ ID NO: 34, 9 |
| | Q136V | SEQ ID NO: 8, 35/SEQ ID NO: 36, 9 |
| | Q136A | SEQ ID NO: 8, 37/SEQ ID NO: 38, 9 |
| | Q136D | SEQ ID NO: 8, 39/SEQ ID NO: 40, 9 |

TABLE 7-continued

| Mutant plasmid | Substituted amino acid | SEQ ID NO of primer |
|---|---|---|
| | Q136E | SEQ ID NO: 8, 41/SEQ ID NO: 42, 9 |
| | Q136G | SEQ ID NO: 8, 43/SEQ ID NO: 44, 9 |
| | Q136W | SEQ ID NO: 8, 45/SEQ ID NO: 46, 9 |

Specifically, PCR was carried out using the primers in Table 7. As a polymerase, Solg™ Pfu-X DNA polymerase (SolGent co., Ltd.) was used, and PCR conditions were as follows: denaturation at 95° C. for 10 minutes; 30 cycles of denaturation at 95° C. for 30 seconds, annealing at 56° C. for 30 seconds, and polymerization at 72° C. for 3 minutes; and polymerization at 72° C. for 5 minutes. As a result, a 712 bp DNA fragment of the 5'-upstream region of the ilvB gene and a 3,310 bp DNA fragment of the 3'-downstream region of the ilvB gene were obtained.

PCR was carried out using the amplified two DNA fragments as a template and primers of SEQ ID NO: 8 and SEQ ID NO: 9. PCR conditions were as follows: denaturation at 95° C. for 10 minutes; 30 cycles of denaturation at 95° C. for 30 seconds, annealing at 56° C. for 30 seconds, and polymerization at 72° C. for 4 minutes; and polymerization at 72° C. for 7 minutes. As a result, 4,010 bp DNA fragments were amplified, each including the mutant ilvB gene encoding the acetohydroxy acid synthase (AHAS) variant in which glutamine at position 136 was substituted with each amino acid of Table 7. The pECCG117 vector (Korean Patent No. 10-0057684) and each of the 4,010 bp ilvBNC DNA fragments obtained by PCR were treated with restriction enzyme BamHI and ligated using a DNA ligase, and then cloned to obtain each plasmid. As a result, 17 ilvB mutant vectors were prepared, each having substitution of glutamine at position 136 with the amino acid of Table 7, and designated as in Table 8.

TABLE 8

| Mutation site | Substituted amino acid | SEQ ID NO of primer |
|---|---|---|
| ilvB 136 mutation | Q136R | pECCG117-ilvB(Q136R)NC |
| | Q136F | pECCG117-ilvB(Q136F)NC |
| | Q136S | pECCG117-ilvB(Q136S)NC |
| | Q136Y | pECCG117-ilvB(Q136Y)NC |
| | Q136C | pECCG117-ilvB(Q136C)NC |
| | Q136P | pECCG117-ilvB(Q136P)NC |
| | Q136H | pECCG117-ilvB(Q136H)NC |
| | Q136L | pECCG117-ilvB(Q136L)NC |
| | Q136I | pECCG117-ilvB(Q136I)NC |
| | Q136T | pECCG117-ilvB(Q136T)NC |
| | Q136K | pECCG117-ilvB(Q136K)NC |
| | Q136V | pECCG117-ilvB(Q136V)NC |
| | Q136A | pECCG117-ilvB(Q136A)NC |
| | Q136D | pECCG117-ilvB(Q136D)NC |
| | Q136E | pECCG117-ilvB(Q136E)NC |
| | Q136G | pECCG117-ilvB(Q136G)NC |
| | Q136W | pECCG117-ilvB(Q136W)NC |

Example 8: Evaluation of L-Isoleucine Productivity of Mutant ilvB Having Acetohydroxy Acid Synthase (AHAS) Activity Each of the 17 mutant plasmids prepared in Example 7 was introduced into the WTΔilvBNC strain prepared in Example 3 by an electric pulse method, and then each was plated on a selection medium containing 25 mg/L of kanamycin to obtain a transformant. Thereafter, a flask test was performed in the same manner as in Example 6. The results are shown in Table 9 below.

TABLE 9

| | L-Isoleucine (g/L) | | |
|---|---|---|---|
| Strain | Batch 1 | Batch 2 | Batch 3 |
| ATCC 13032 hom(R407H) ilvA(F383A) | 0.23 | 0.21 | 0.20 |
| ATCC 13032 hom(R407H) ilvA(F383A) ΔilvBNC | 0 | 0 | 0 |
| ATCC 13032 hom(R407H) ilvA(F383A) ΔilvBNC/ pECCG117-ilvBNC WT | 0.21 | 0.20 | 0.19 |
| ATCC 13032 hom(R407H) ilvA(F383A) ΔilvBNC/ pECCG117-ilvB(Q136N)NC | 3.01 | 3.12 | 3.20 |
| ATCC 13032 hom(R407H) ilvA(F383A) ΔilvBNC/ pECCG117-ilvB(Q136R)NC | 2.87 | 3.00 | 2.95 |
| ATCC 13032 hom(R407H) ilvA(F383A) ΔilvBNC/ pECCG117-ilvB(Q136F)NC | 3.11 | 3.15 | 3.04 |
| ATCC 13032 hom(R407H) ilvA(F383A) ΔilvBNC/ pECCG117-ilvB(Q136S)NC | 1.89 | 0.86 | 0.91 |
| ATCC 13032 hom(R407H) ilvA(F383A) ΔilvBNC/ pECCG117-ilvB(Q136Y)NC | 2.96 | 2.76 | 2.74 |
| ATCC 13032 hom(R407H) ilvA(F383A) ΔilvBNC/ pECCG117-ilvB(Q136C)NC | 2.56 | 2.48 | 2.61 |
| ATCC 13032 hom(R407H) ilvA(F383A) ΔilvBNC/ pECCG117-ilvB(Q136P)NC | 1.45 | 1.23 | 1.34 |
| ATCC 13032 hom(R407H) ilvA(F383A) ΔilvBNC/ pECCG117-ilvB(Q136H)NC | 2.99 | 2.96 | 2.98 |
| ATCC 13032 hom(R407H) ilvA(F383A) ΔilvBNC/ pECCG117-ilvB(Q136L)NC | 3.02 | 3.10 | 3.06 |
| ATCC 13032 hom(R407H) ilvA(F383A) ΔilvBNC/ pECCG117-ilvB(Q136I)NC | 2.45 | 2.41 | 2.39 |
| ATCC 13032 hom(R407H) ilvA(F383A) ΔilvBNC/ pECCG117-ilvB(Q136T)NC | 0.81 | 0.83 | 0.79 |
| ATCC 13032 hom(R407H) ilvA(F383A) ΔilvBNC/ pECCG117-ilvB(Q136K)NC | 3.01 | 3.05 | 3.00 |
| ATCC 13032 hom(R407H) ilvA(F383A) ΔilvBNC/ pECCG117-ilvB(Q136V)NC | 1.23 | 1.25 | 1.19 |
| ATCC 13032 hom(R407H) ilvA(F383A) ΔilvBNC/ pECCG117-ilvB(Q136A)NC | 3.00 | 3.01 | 2.94 |
| ATCC 13032 hom(R407H) ilvA(F383A) ΔilvBNC/ pECCG117-ilvB(Q136D)NC | 2.75 | 2.81 | 2.83 |
| ATCC 13032 hom(R407H) ilvA(F383A) ΔilvBNC/ pECCG117-ilvB(Q136E)NC | 1.01 | 1.01 | 0.99 |
| ATCC 13032 hom(R407H) ilvA(F383A) ΔilvBNC/ pECCG117-ilvB(Q136G)NC | 1.02 | 0.98 | 1.05 |
| ATCC 13032 hom(R407H) ilvA(F383A) ΔilvBNC/ pECCG117-ilvB(Q136W)NC | 2.65 | 2.67 | 2.63 |

As shown in Table 9, it was confirmed that all mutant strains, each including the mutant amino acid at position 136 of ilvB, produced a high level of L-isoleucine as compared with the wild-type. These results indicate that substitution of the amino acid at position 136 of ilvB with another amino acid is important for increasing L-isoleucine productivity.

The above results suggest that the variants of the present disclosure increase L-isoleucine production.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A protein variant having acetohydroxy acid synthase (AHAS) activity comprising an amino acid sequence having at least 90% sequence identity to SEQ ID NO: 1, wherein glutamine, which is an amino acid at a position corresponding to position 136 in the amino acid sequence of SEQ ID NO: 1, is substituted with an amino acid other than glutamine.

2. The protein variant having acetohydroxy acid synthase activity of claim 1, wherein the amino acid at the position corresponding to position 136 is substituted with asparagine, arginine, phenylalanine, serine, tyrosine, cysteine, proline, histidine, leucine, isoleucine, threonine, lysine, valine, alanine, aspartic acid, glutamic acid, glycine, or tryptophan.

3. The protein variant of claim 1, wherein the protein variant comprises the af amino acid sequence of SEQ ID NO: 12, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, or SEQ ID NO: 63.

4. A polynucleotide encoding the protein variant of claim 1.

5. A vector comprising the polynucleotide of claim 4.

6. A microorganism comprising the protein variant of claim 1.

7. The microorganism of claim 6, wherein the microorganism produces L-isoleucine.

8. The microorganism of claim 6, wherein the microorganism belongs to the genus *Corynebacterium* (*Corynebacterium* sp.) or the genus *Escherichia* (*Escherichia* sp.).

9. A method of producing L-isoleucine, the method comprising culturing the microorganism of claim 6 in a medium.

10. The method of claim 9, further comprising recovering L-isoleucine from the cultured microorganism or the medium.

11. A polynucleotide encoding the protein variant of claim 2.

12. A polynucleotide encoding the protein variant of claim 3.

13. A microorganism comprising the protein variant of claim 2.

14. A microorganism comprising the protein variant of claim 3.

15. The protein variant of claim 1, wherein the protein variant comprises the amino acid sequence of SEQ ID NO: 12.

16. The protein variant of claim 1, wherein the protein variant comprises the amino acid sequence of SEQ ID NO: 48, SEQ ID NO: 54, or SEQ ID NO: 57.

17. The protein variant of claim 1, wherein the protein variant comprises the amino acid sequence of SEQ ID NO: 47, SEQ ID NO: 53, or SEQ ID NO: 59.

18. The protein variant of claim 1, wherein the protein variant comprises the amino acid sequence of SEQ ID NO: 50, SEQ ID NO: 51, SEQ ID NO: 55, SEQ ID NO: 60, or SEQ ID NO: 63.

19. The protein variant of claim 1, wherein the protein variant comprises the amino acid sequence of SEQ ID NO: 49, SEQ ID NO: 52, SEQ ID NO: 58, SEQ ID NO: 61, or SEQ ID NO: 62.

20. The protein variant of claim 1, wherein the protein variant comprises the amino acid sequence of SEQ ID NO: 56.

* * * * *